Figure 1:
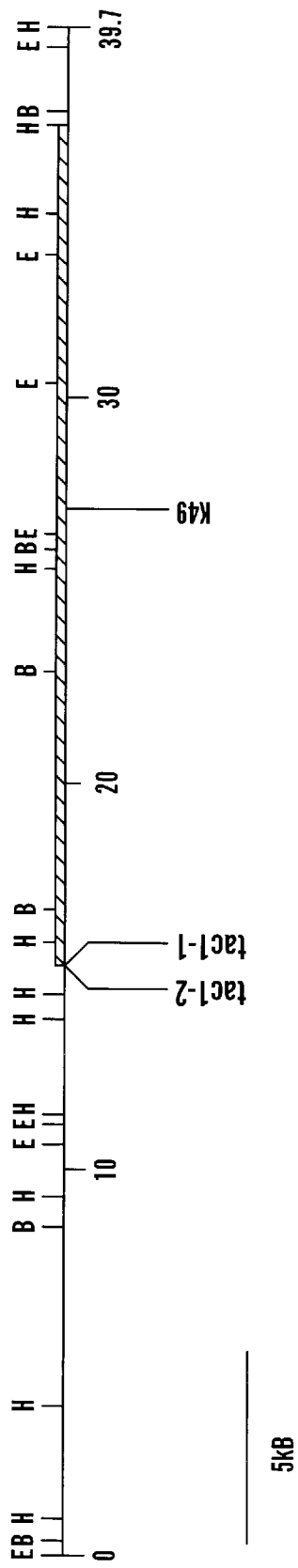

United States Patent [19]
Beer et al.

[11] Patent Number: 5,849,868
[45] Date of Patent: Dec. 15, 1998

[54] ELICITOR OF THE HYPERSENSITIVE RESPONSE IN PLANTS

[75] Inventors: Steven V. Beer; Zhong-Min Wei; David W. Bauer; Alan Collmer; Sheng-Yang He; Ron Laby, all of Ithaca, N.Y.

[73] Assignee: Cornell Research Foundation, Inc., Ithaca, N.Y.

[21] Appl. No.: 200,724

[22] Filed: Feb. 23, 1994

Related U.S. Application Data

[63] Continuation of Ser. No. 907,935, Jul. 1, 1992, abandoned.
[51] Int. Cl.⁶ .............................. C07K 14/00; C07K 5/00; C07K 1/00; C07K 17/00
[52] U.S. Cl. ........................ 530/350; 530/324; 530/326; 530/823; 530/825
[58] Field of Search ..................................... 530/324, 326, 530/823, 825, 350

[56] References Cited

U.S. PATENT DOCUMENTS

| | | |
|---|---|---|
| 4,569,841 | 2/1986 | Liu . |
| 4,597,972 | 7/1986 | Taylor . |
| 4,601,842 | 7/1986 | Caple et al. . |
| 4,740,593 | 4/1988 | Gonzalez et al. . |
| 4,851,223 | 7/1989 | Sampson . |
| 4,886,825 | 12/1989 | Ruess et al. . |
| 4,931,581 | 6/1990 | Schurter et al. . |
| 5,057,422 | 10/1991 | Bol et al. . |
| 5,061,490 | 10/1991 | Paau et al. . |
| 5,135,910 | 8/1992 | Blackburn et al. . |
| 5,217,950 | 6/1993 | Blackburn et al. . |
| 5,243,038 | 9/1993 | Ferrari et al. ........................ 536/23.1 |
| 5,244,658 | 9/1993 | Parke . |
| 5,260,271 | 11/1993 | Blackburn et al. . |
| 5,348,743 | 9/1994 | Ryals et al. . |
| 5,494,684 | 2/1996 | Cohen . |
| 5,523,311 | 6/1996 | Schurter et al. . |
| 5,550,228 | 8/1996 | Godiard et al. ........................ 536/24.1 |
| 5,552,527 | 9/1996 | Godiard et al. ........................ 530/379 |
| 5,569,830 | 10/1996 | Bennett et al. . |
| 5,708,139 | 1/1998 | Collmer et al. . |

FOREIGN PATENT DOCUMENTS

| | | |
|---|---|---|
| WO 95/19443 | 7/1995 | European Pat. Off. . |
| WO 94/01546 | 1/1994 | WIPO . |
| WO 94/26782 | 11/1994 | WIPO . |

OTHER PUBLICATIONS

Ingrid, M. et al. (1988) Purification and primary structure of a necrosis–inducing peptide from the apoplastic fluids of tomato infected with *C. fulvum* (syn. *Fulvia fulva*). *Physiol. Molec. Plant Pathol.* 33, 59–67. see entire article.

Huang et al., "Molecular Cloning of a *Pseudomonas syringae* pv. syringae Gene Cluster That Enables *Pseudomonas fluorescens* To Elicit the Hypersensitive Response in Tobacco Plants," *Journal of Bacteriology*, 170(10):4748–4756 (1988).

Laby et al., "Cloning and Preliminary Characterization of an HRP Gene Cluster *Erwinia Amylovora*," *Phytopathology*, 79(10):607 (1989).

van Kan et al., "Cloning and Characterization of cDNA of Avirulence Gene avr9 of the Fungal Pathogen *Cladosporium fulvum*, Causal Agent of Tomato Leaf Mold," *Molecular Plant–Microbe Interactions*, 4(1):52–59 (1991).

Keen et al., "Inhibition of the Hypersensitive Reaction of Soybean Leaves to Incompatible Pseudomonas spp. by Blasticidin S, or elevated Temperature," *Physiological Plant Pathology*, 18:325–337 (1981).

Hippe et al., "In Situ Localization of a Foreign Protein in Transgenic Plants by Immunoelectron Microscopy Following High Pressure Freeze Substitution and Low Temperature Embedding," *European Journal of Cell Biology*, 50:230–234 (1989).

James et al., "Genetic Transformation of Apple (*Malus pumila* Mill.) Using a Disarmed Ti–binary Vector," *Plant Cell Reports*, 7:658–661 (1989).

Willis et al., "hrp Genes of Phytopathogenic Bacteria," *Molecular Plant–Microbe Interactions*, 4:(2) 132–138 (1991).

Lerner "Tapping the Immunological Repertoire to Produce Antibodies of Predetermined Specificity," *Nature*, 299:592–596 (1982).

Hiatt et al., "Production of Antibodies in Transgenic Plants," 342:76–78 (1989).

Collinge et al., "Plant Gene Expression in Response to Pathogens," *Plant Molecular Biology*, 9:389–410 (1987).

Wu et al., "Cloning, Genetic Organization, and Characterization of a Structural Gene Encoding Bacillopeptidase F from *Bacillus subtilis*," *The Journal of Biological Chemistry*, 265(12):6845–6850 (1990).

Waldmann, "Monoclonal Antibodies in Diagnosis and Therapy," *Science*, 252:1657–1662 (1991).

Dow et al., "Extracellular Proteases from *Xanthomonas campestris* pv. Campestris, the Black Rot Pathogen," *Applied and Enviromental Microbiology*, 56(10):2994–2998 (1990).

Shields, "Towards Insect–Resistant Plants," *Nature*, 328:12–13 (1987).

Beer et al., "Are Harpins Universal Elicitors of the Hypersensitive Response of Phytopathogenic Bacteria?," *Advances in Molecular Genetics of Plant–Microbe Interactions*, 2:281–286 (1992).

Lindgren et al., "Gene Cluster of *Pseudomonas Syringae* pv. Phaseolicola Controls Pathogenicity of Bean Plants and Hypersensitivity on Nonhost Plant," 168(2):512–522 (1986).

(List continued on next page.)

Primary Examiner—Nita Minnifield
Attorney, Agent, or Firm—Nixon, Hargrave, Devans & Doyle

[57] ABSTRACT

The nucleic acid and amino acid sequences for proteinaceous elicitors of the plant defense reaction known as the hypersensitive response are described along with methods for preparation and processes for inactivation.

11 Claims, 2 Drawing Sheets

OTHER PUBLICATIONS

Huynh et al., "Bacterial Blight of Soybean: Regulation of a Pathogen Gene Determining Host Cultivar Specificity," *Science,* 245:1374–1377.

Milat et al., "Physiological and Structural Changes in Tobacco Leaves Treated with Cryptogein, a Proteinaceous Elicitor from *Phytophthora cryptogea,*" *Phytopathology,* 81(11):1364–1368.

Atkinson et al., "The Hypersensitive Reaction of Tobacco to *Pseudomonas Syringae* pv. *pisi*[1]," *Plant Physiol.,* 79:843–847 (1985).

Benvenuto et al., "'Phytoantibodies': A General Vector for the Expression of Immunoglobulin Domains in Transgenic Plants," *Plant Molecular Biology,* 17:865–874 (1991).

Quigley et al., "Nucleotide Sequence and Expression of a Novel Glycine–Rich Protein Gene from *Arabidopsis Thaliana,*" *Plant Molecular Biology,* 17:949–952 (1991).

Huang et al., "Isolation and Purification of a Factor from *Pseudomonas Solanacearum* That Induces a Hypersensitive–like Response in Potato Cells," *Molecular Plant–Microbe Interactions,* 2(3):132–138 (1989).

Bauer et al., "Further Characterization of an hrp Gene Cluster of *Erwinia Amylovora,*" 45(5):493–499 (1991).

Stryer, "Enzymes are Highly Specific," *Biochemistry,* p. 116 (1975).

Ruberti et al., "A Novel Class of Plant Proteins Containing a Homeodomain with a Closely Linked Leucine Zipper Motif," *The EMBO Journal,* 10(7):1787–1791 (1991).

Shatzman et al., "Expression, Identification, and Characterization of Recombinant Gene Products in *Escherichia coli,*" *Methods in Enzymology,* 152:661–673 (1987).

Staskawicz et al., "Cloned Avirulence Gene of *Pseudomonas Syringae* pv. *glycinea* Race–specific Incompatiblity on *Glycine max* (L.) Merr.," *Proc. Natl. Acad. Sci.,* 81:6024–6028 (1984).

Wei et al., "Harpin, Elicitor of the Hypersensitive Response Produced by the Plant Pathogen *Erwinia Amylovora,*" *Science,* 257:85–88 (1992).

Bauer et al., "Cloning of a Gene from *Erwinia Amylovora* Involved in Induction of Hypersensitivity and Pathogenicity," *Plant Pathogenic Bacteria,* 425–429 (1987).

Beer et al., "The HRP Gene Cluster of *Erwinia Amylovora,*" *Advances in Molecular Genetics of Plant–Microbe Interactions,* 1:53–60 (1991).

Walters et al., "Gene for Pathogenicity and Ability to Cause the Hypersensitive Reaction Cloned from *Erwinia Amylovora,*" *Physiological and Molecular Plant Pathology,* 36:509–521 (1990).

Steinberger et al., "Creation and Complementation of Pathogenicity Mutants of *Erwinia Amylovora,*" *Molecular Plant–Microbe Interactions,* 1(3):135–144 (1988).

Beer et al., "The Hypersensitive Response is Elicited by *Escherichia Coli* Containing a Cluster of Pathogenicity Genes from *Erwinia Amylovora,*" *Phytopathology,* 79(10):169 (1989).

Sandhu, "Crit. Rev. in Biotech," (92–review) 12:437–462.

Laby et al., *Molecular Plant–Microbe Interactions,* 5(5):412 (1992).

Bauer et al., "*Erwinia chrysanthemi* Genes and their Involvement in Elicitation of the Hypersensitive Response," Sixth Internationaly Symposium on Molecular Plant Microbe Interactions, Abstract No. 146 (Jul. 1992).

Huang et al., "Characterization of the hrp Cluster from *Pseudomonas syringae* pv. syringae 61 and TnphoA Tagging of Genes Encoding Exported or Membrane–Spanning Hrp Proteins," *Molec. Plant–Microbe Interact.,* 4(5):469–476 (1991).

Huang et al., "The *Pseudomonas syringae* pv. syringae 61 hrpH Product, and Envelope Protein Required for Elicitation of the Hypersensitive Response in Plants," *J. of Bacteriology,* 174(21):6878–6885 (1992).

Kelman, A., "The Relationship of Pathogenicity in Pseudomonas Solanacearum To Colony Appearance on a Tetrazolium Medium," *Phytopathology,* 44:693–695 (1954).

Winstead et al., "Inoculation Techniques For Evaluating Resistance to Pseudomonas Solanacearum," *Phytopathology,* 42:628–634 (1952).

Ahl et al., "Iron Bound–Siderophores, Cyanic Acid, and Antibiotics Involved in Suppression of *Thielaviopsis basiocola* by a *Pseudomonas fluorescens* Strain," *J. Pathology,* 116:121–134 (1986).

Anderson et al., "Responses of Bean to Root Colonization with *Pseudomonas putida* in a Hydroponic System," *Phytopathology,* 75(9)992–995 (1985).

Gardner et al., "Growth Promotion and Inhibition by Antibiotic–Producing Fluorescent Pseudomonads on Citrus Roots," *Plant and Soil,* 77:103–113 (1984).

Kloepper, "Effect of Seed Piece Inoculation with Plant Growth–Promoting Rhizobacteria on Populations of *Erwinia carotovora* on Potato Roots and In Daughter Tubers," *Phytopathology,* 73:217–219 (1983).

Kloepper et al., "Plant Growth–Promoting Rhizobacteria on Canola (Rapseed)," *Plant Disease* 72(1):42–46 (1988).

Kloepper et al., "Enhanced Plant Growth by Siderophores Produced by Plant Growth–Promoting Rhizobacteria," *Nature,* 286:885–886 (1980).

Kloepper et al., "Pseudomonas Siderophores: A Mechanism Explaining Disease–Suppressive Soils," *Current Microbiology,* 4:317–320 (1980).

Kloepper et al., "Emergence–Promoting Rhizobacteria: Description and Implications for Agriculture," In: *Iron, Siderophores, and Plant Disease,* Swinborne (ed), Plenum, NY, 155–164 (1986).

Kloepper et al., "Relationships of in vitro Antibiosis of Plant Growth–Promoting Rhizobacteria to Plant Growth and the Displacement of Root Microflora," *Phytopathology,* 71(10):1020–1024 (1981).

Kloepper et al., "Effects of Rhizosphere Colonization by Plant Growth–Promoting Rhizobacteria on Potato Plant Development and Yield," *Phytopathology,* 70(11):1078–1082 (1980).

Kloepper et al., "Plant Growth Promotion Mediated by Bacterial Rhizosphere Colonizers,"In: *The Rhizosphere and Plant Growth,* Keister et al. (eds), 315–326 (1991).

Lifshitz et al., "Growth Promotion of Canola (rapseed) Seedlings by a Strain of *Pseudomonas putida* Under Gnotobiotic Conditions," *Microbiol.* 33:390–395 (1987).

Loper et al., "Influence of Bacterial Sources of Indole–3–acetic Acid on Root Elongation of Sugar Beet," *Phytopathology,* 76(4):386–389 (1986).

Schroth et al., "Disease–Suppressive Soil and Root–Colonizing Bacteria," *Science,* 216:1376–1381 (1982).

Stutz et al., "Naturally Occurring Fluorescent Pseudomonads Involved in Suppression of Black Root Rot of Tobacco," *Phytopathology,* 76(4):181–185 (1986).

Wei et al., "Induction of Systemic Resistance of Cucumber to *Colletotrichum orbiculare* by Select Strains of Plant Growth–Promoting Rhizobacteria," *Phytopathology*, 81:1508–1512 (1991).

Weller, "Biological Control of Soilborne Plant Pathogens in the Rhizosphere with Bacteria," *Ann. Rev. Phytopathol.*, 26:379–407 (1988).

Young et al., "PGPR: Is There a Relationship Between Plant Growth Regulators and the Stimulation of Plant Growth or Biological Activity?," pp. 182–186.

Malamy et al., "Salicylic Acid: A Likely Endogenous Signal in the Resistance Response of Tobacco to Viral Infection," *Science*, 250:1002–1004 (1990).

Bonnet et al., "Induction de nécroses foliaires, de protéines b et de résistance dans les interactions tabac Phytophthora," *Agronomie*, 6(9):829–37 (1986).

Gallitelli et al., "Satellite–Mediated Protection of Tomato Against Cucumber Mosaic Virus: II. Field Test Under Natural Epidemic Conditions in Southern Italy," *Plant Disease*, 75(1):93–95 (1991).

Montasser et al., "Satellite–Mediated Protection of Tomato Against Cucumber Mosaic Virus: I. Greenhouse Experiments and Stimulated Epidemic Conditions in the Field," *Plant Disease*, 75(1):86–92 (1991).

Marks R.J., "Varietal Resistance to Potato Cyst Nematode," *Agricultural Entomology*, (1979) 63–64, 66–67.

Walton et al., "Host–Selective Toxins and Disease Specificity: Perspectives and Progress," *Annu. Rev. Phytopathol.*, 31:275–303.

Godiard et al., "Differential Regulation in Tobacco Cell Suspensions of Genes Involved in Plant–Bacteria Interactions by Pathogen–Related Signals," *Plant Molecular Biology*, 17:409–13 (1991).

Ricci et al., "Structure and Activity of Proteins from Pathogenic Fungi Phytophthora Eliciting Necrosis and Acquired Resistance in Tobacco," *Eur. J. Biochem.*, 183:555–63 (1989).

Lakhmatova I.T., "Induction of Plant Resistance to Viral Diseases: Application of Vaccination," *Sel'skokhozyaistvennaya* 3:39–51 (1991) English/Abstract.

*Biologicheskii Zhurnal Armenii*, 31(3):305–09 (1978) Abstract/English.

Lakhmatova I.T., "Using Biologically Active Substances to Induced Plant Resistance to Viruses Immunization," *Biologiya*, 3:13–22 (1992).

Ricci et al., "Differential Production of Parasiticein, an Elicitor of Necrosis and Resistance in Tobacco, by Isolates of Phytophthora parasitica," *Plant Pathology*, 41:298–307 (1992).

Keen et al., "Bacteria Expressing Avirulence Gene D Produce a Specific Elicitor of the Soybean Hypersensitive Reaction," *Molecular Plant–Microbe Interactions*, 3(2):112–21 (1990).

Collmer et al., "*Erwinia chyrsanthemi* and *Pseudomonas syringae*: Plant Pathogens Trafficking in Extracellular Virulence Proteins," *Current Topics in Microbiology and Immunology*, 192:43–78 (1994).

Wei et al., "Induction of Systemic Resistance with Seed Treatment by PGPR Strains," *Bulletin of the International Organization for Biological and Integrated Control of Noxious Animals and Plants, Western Palearctic Regional Section*, pp. 191–194 (1991).

Dean et al., "Immunisation Against Disease: The Plant Fights Back," *British Mycological Society Symposium*, pp. 383–410 (1988).

Wieringa–Brants et al., Induced Resistance in Hypersensitive Tobacco Against Tobacco Mosaic Virus by Injection of Intercellular Fluid from Tobacco Plants with Systemic Acquired Resistance, *Phytopathology*, 118:165–170 (1987).

Ahn et al., "Effects of Chilling Periods on the Growth and Yield of Strawberry (*Fragaria grandifloro* EHRH) in Forcing Culture," *Res. Rept. RDA (Hort.)*, 27(1):17–26 (1985).

ELICITOR OF THE HYPERSENSITIVE RESPONSE IN PLANTS

This application is a continuation of application Ser. No. 07/907,935, filed Jul. 1, 1992, now abandoned.

Partial support for the research which led to the making of the present invention was provided by funds from the United States Department of Agriculture. Accordingly, the United States government has certain statutory rights to this invention under 35 USC 200 et seq.

Plants, as well as humans and animals, suffer injury and losses due to infection by bacteria. On a worldwide basis, bacteria classified in the genera *Erwinia, Pseudomonas* and *Xanthomonas* are responsible for most losses due to bacterial plant pathogens. Many of the bacterial diseases of plants cause farmers great losses on a sporadic basis. The losses result from death, disfigurement or reduced productivity of affected plants.

Many bacterial pathogens of plants exhibit a marked degree of specificity towards the plants that they infect. For example, *Erwinia amylovora* infects apples, pears and related plants of the family Rosaceae. Other plants do not become diseased when exposed to *E. amylovora*. However, when sufficient cells of *E. amylovora* are introduced into leaf tissue of the other plants, the mesophyll tissue collapses within hours. This collapse has been called the hypersensitive response (HR), and it is considered a defense reaction of plants since, during the HR, the bacteria are delimited within the collapsed tissue, eventually die, and thus do not cause much damage to the plant as a whole.

The genes that bacterial plant pathogens require for HR-eliciting ability, are called hrp genes, for hypersensitive reaction and pathogenicity, are also required for causing disease. However, the products of hrp genes and how they function in elicitation of the HR, and in disease development, remained unknown prior to the present invention. The present invention concerns products of hrp genes (elicitors) that are responsible for the collapse seen in the HR and are required for disease development.

Interactions between bacterial pathogens and their plant hosts generally fall into two categories: (1) compatible (pathogen-host), leading to intercellular bacterial growth, symptom development and disease development in the host plant; and (2) incompatible (pathogen-nonhost), resulting in the hypersensitive response, a particular type of incompatible interaction occurring, without progressive disease symptoms. During compatible interactions on host plants, bacterial populations increase dramatically and progressive symptoms occur; during incompatible interactions bacterial populations do not increase, and progressive symptoms do not occur.

The hypersensitive response of higher plants is characterized by the rapid, localized collapse and death of tissues containing an incompatible pathogen (a microorganism that is pathogenic only on other plants) and is associated with the defense of plants against many bacteria, fungi, nematodes, and viruses [see Phytopathogenic Prokaryotes, (M. S. Mount and G. H. Lacy eds.) Academic Press, New York. pp 149–177 (1982)]. Elicitation of the hypersensitive response by bacteria was first demonstrated in 1963 when the intercellular spaces of tobacco leaves were infiltrated with $10^7$ cells/ml of an incompatible pathogen. The infiltrated areas collapsed within 24∝48 hours and ceased to support bacterial multiplication [see Nature 199:299 (1963)]. Thus, in the HR, the pathogen is localized and further growth is restricted.

The technique used in the laboratory to demonstrate the HR is straight-forward. The intercellular spaces of tobacco leaves are infiltrated by first puncturing a sector on a leaf with a common straight dissecting needle. Then a 1-ml capacity syringe (without a needle), containing 0.1–0.5 ml of a bacterial cell suspension (usually $10^7$–$10^8$ viable cells/ml) of bacteria is pressed against one side of the leaf directly over the puncture. While pressing a finger on the opposite side of the leaf to stabilize it and to prevent liquid from leaking out of the punctured area, the syringe plunger is pressed gently to introduce the bacterial suspension into the leaf. Infiltration is considered successful when a water-soaked area approximately 1–4 cm² appears in the leaf.

A common hypothesis proposed to explain the mechanism of hypersensitive reaction induction involves the production by bacteria of a specific elicitor that reacts with a specific receptor on the plant cell. However, the molecular basis (gene and gene product) for this response to potential pathogens had been unknown prior to the present invention in spite of continued research by plant pathologists since the HR first was described in 1963.

Physiological and genetic observations suggest that the same bacterial factor that elicits the hypersensitive response in nonhosts is also required for pathogenicity in hosts.

Production of the elicitor of the hypersensitive response is controlled by a cluster of several hrp genes, which are highly conserved, and often interchangeable, among many species of plant pathogenic bacteria. Although individual and several hrp genes have been cloned by others, functional clusters of hrp genes have been cloned only from *Erwina amylovora* and *Pseudomonas syringae*. These clusters have been shown to confer on nonpathogenic bacteria the ability to elicit the hypersensitive response in tobacco and other leaves [see Mol. Plant-Microbe Interact. 4:132 (1991); J. Bacteriol 170:4748 (1988); and Beer et al., Advances in Molecular Genetics of Plant-Microbe Interactions (H. Hennecke and D.P.S. Verma eds.) Kluwer Academic Publishers, Boston, pp 53–60 (1991)].

The elicitor, according to the present invention, was initially isolated and purified from *E. coli* DH5α(pCPP430), and later from a wild-type strain of *E. amylovora*, the bacterium that causes a disease of rosaceous plants, such as apple and pear, known as fire blight. According to the present invention, the name "harpin" is proposed for the hypersensitive response elicitor from *E. amylovora*; this elicitor is considered to be the archetype for a family of proteinaceous HR elicitors that are produced by many different phytopathogenic bacteria.

It is thus one aspect of this present invention to describe specific elicitor proteins isolated from bacteria, which when applied to nonhost plants, cause a toxic response that is similar to the response elicited by living cells of the bacteria that produced the proteins. A further aspect of this present invention is to isolate and describe the genes that encode the elicitor proteins, which might be used to cause plants or other organisms to produce elicitor protein, which would exert its toxic effects in a precise controlled manner.

A further aspect of this present invention is to provide sufficient characterization, and identification of these proteins to allow design and development of techniques that will inactivate, destroy, or bind with these proteins. This aspect is desirable because it is known the same proteins are required by the bacteria that produce them in order to cause disease in host plants of the bacteria. Neutralizing the toxic effects of the proteins neutralizes their roles in disease and reduces disease in plants.

A still further aspect of the present invention is to develop antibodies against these proteins, sequence the antibodies produced, construct nucleic acid sequences which when inserted properly into the genome of a plant would cause the plant to express the antibody and thus prevent bacteria from causing disease in plants.

One portion of the present invention is based on the identification of a particular hrp gene of the hrp gene cluster of *Erwinia amylovora*. That particular gene is transcribed and translated to yield the proteinaceous elicitor of the hypersensitive response. Another portion of the present invention deals with the identification of homologous genes from *Erwinia, Xanthomonas*, and *Pseudomonas* species that encode similar proteins to the HR elicitor from *E. amylovora*. Prior to the making of the present invention, the isolation of a proteinaceous elicitor of the hypersensitive response had not been reported. Thus, another portion of the present invention is a description of techniques for isolation and purification of a proteinaceous elicitor of the hypersensitive response. An additional portion of this invention concerns the genetic manipulation of the genes encoding the HR-elicitor proteins to enhance production of harpin.

Therefore, it may be summarized that the various portions and aspects of the present invention relate to providing prophylaxis against *Erwinia amylovora*, the causative agent of fire blight of apple, pear, and other rosaceous plants. In addition, the present invention broadly relates to providing prophylaxis to bacteria of the genera *Erwinia, Pseudomonas* and *Xanthomonas* which cause other diseases of a variety of plants.

In order to provide a clear understanding of the present invention, the following terms relating to the bacterial strains, cosmids and plasmids referred to in the description of the present invention are provided.

| | |
|---|---|
| DH5α | A laboratory strain of *Escherichia coli* used routinely for cloning; |
| Ea321 | Wild-type strain of *Erwinia amylovora* from which all mutants and clones were derived; |
| Ea321T143 | Hrp mutant containing transposon Tn5 that was used to screen a cosmid library (in pCPP9 vector) for restoration of Hrp function. This screening resulted in the identification of cosmid pCPP430. (This mutant has an insertion in one of the hrp genes, not hrpN; the effect of the insertion is to prevent expression of harpin by mutagenesis of the operon). |
| Ea321K49 | Hrp mutant containing the Tn10mini-kan transposon which is inserted in an hrp gene involved in regulation of harpin production. |
| Ea321T5 | Hrp mutant containing the hrpN gene that was mutaenized with the Tn5tac1 nonpolar transposon. (This mutant of Ea321 has an insertion in the gene that encodes harpin). |
| pCPP9 | A cosmid vector constructed for the cloning of DNA of *E. amylovora*. The vector portion of pCPP430. |
| pCPP430 | Cosmid containing 46.5 kb of Ea321 DNA that includes the whole hrp gene cluster of Ea321. This cosmid bestows on *E. coli* the ability to elicit the HR, and restore the Hrp phenotype to all Hrp mutants of *E. amylovora*. Clone from which hrpN was derived. |
| pCPP1084 | Plasmid containing a 1.3 kb HindIII fragment from pCPP430, which includes the whole hrpN (1155 base pairs). The vector is pBluescript M13+. |
| pCPP50 | A plasmid developed by modifying pINIII$^{113}$-A2 of Masui et al. (Bio/Technology, January 1984 pp. 81–85). A fragment of the original was deleted and a fragment from pBluescript was inserted. The modifications were made to create a vector more suitable for harpin production. |
| pCPP2139 | Plasmid that when in *E. coli* results in superproduction of harpin. Constructed by cloning the hrpN gene from pCPP430 into pCPP50. |
| pBluescript M13+ | A plasmid routinely used for subcloning and sequencing of DNA. Used also for in vitro expression of protein from cloned DNA. |

In addition, these and other terms used throughout this description may be found in Molecular Plant-Microbe Interactions 4(5):493 (1991) and Advances in Molecular Genetics of Plant-Microbes Interaction 1:53 (1991).

Both *E. coli* DH5α(pCPP1084) and *E. amylovora* Ea321 have been deposited with the American Type Culture Collection in Rockville, Md. Their deposit number are ATCC 69021 and ATCC 49947, respectively. The deposit of ATCC 69021 has been made under the Budapest Treaty, and cultures will be made available in accordance with the provisions of this treaty.

The various aspects regarding the identification, isolation, purification and characterization of the HR elicitor and gene according to the present invention can be more clearly understood from the following figures and examples, all of which are provided for purposes of clarifying the present invention and not for limiting the scope thereof.

FIG. 1 is a restriction endonuclease map of the hrp cluster of *Erwinia amylovora*; and FIG. 2 depicts the changes in pH of a bathing solution of tobacco cell-suspension cultures.

More particularly, FIG. 1 represents the restriction endonuclease map of the hrp cluster of *Erwinia amylovora* in which “E” designates EcoRI, “H” designates HinduIII, and “B” designates BamHI restriction sites. The vertical lines indicate the location of transposon insertions that have been tested for their effects on the ability to elicit the HR and to be pathogenic on pear. Metabolically active cells of *Erwinia amylovora* Ea321 [see Molecular Plant-Microbe Interactions 1(3):135 (1988)] and *E. coli* DH5α(pCPP430) with all indicated insertions fail to elicit the hypersensitive reaction in tobacco. The region encompassed by all indicated insertions is essential also for the elicitation of a $K^+/H^+$ exchange reaction of tobacco cell suspension cultures. Derivatives of Ea321 containing all the indicated insertions are not pathogenic to pear.

More particularly in respect to FIG. 2, the control values (no additive) were subtracted prior to graphing. Open squares depict harpin (60 nM); open circles depict cells of *E. coli* DH5α(pCPP430) ($5\times10^7$ cells/ml); filled squares depict cells of *E. amylovora* Ea321 ($5\times10^7$ cells/ml; triangles depict cells of *E. coli* DH5α(pCPP430K49) ($5\times10^7$ cells/ml); diamonds depict cells of *E. amylovora* Ea321K49 ($5\times10^7$ cells/ml); and filled circles depict cells of *E. coli* DH5α(pCPP9) ($5\times10^7$ cells/ml). Tobacco cell-suspension cultures were shaken at room temperature with the indicated preparations. The pH was measured at the intervals indicated. All preparations that elicited HR in tobacco leaves also caused a pH increase in the tobacco cell-suspension culture medium.

EXAMPLE I

Plasmid pCPP430 was identified from a library of genomic DNA of the wild-type strain of *E. amylovora*, known in our laboratory as Ea321, and has been deposited in the American Type Culture Collection as 49947. The strain was received in 1978 from the French National Collection of Phytopathogenic bacteria, in which it is known as CNFB 1367. Genomic DNA was isolated and digested with Sau3A, ligated into the cosmid vector of pCPP9 previously digested with BamHI, packaged and transfected into *E. coli* strain ED8767 according to procedures previously described [see Mol. Plant-Microbe Int. 1:135 (1988)]. The resulting cosmids were mobilized into strains by conjugation with the aid of the helper plasmid pRK2013 [Bauer, D. W., Molecular genetics of pathogenicity of *Erwinia amylovora*: techniques, tools and their application. Ph.D. thesis. Cornell University, Ithaca, N.Y. (1989)].

The resulting library was diluted and spread on plates of nutrient agar containing both spectinomycin and kanamycin 50 μgm/ml final concentration. Plates containing about 500 colonies, after incubation at 37° for 24 hr, were selected when the diameter of each colony was 0.5–1.0 mm. The colonies from these plates were replica-stamped onto plates containing Luria-Bertani agar (LA) on which 0.1 ml of a suspension of strain Ea321T143 previously had been spread. Ea321T143 is a Tn10-induced Hrp⁻ mutant strain of Ea321; it is not pathogenic to pear fruit and does not elicit the HR in tobacco and other plants. It had been grown to O.D.$_{620}$=1.3 in Luria broth plus tetracycline (10 μgm/ml). The LA plates were incubated for 5 hr at 28° C. and the growth on these plates were replica-plated on to a minimal medium for the growth of *Erwinia amylovora*, which contained glucose 2 g/l, asparagine 1.5 g/l. sodium citrate 0.25 g/l, MgSO$_4$ 5 mg/l, nicotinic acid 0.25 g/l, (NH$_4$)$_2$SO$_4$ 1 g/l, K2HPO$_4$ 3.51 g/l, KH$_2$PO$_4$ 1.51 g/l, and 50 mg/l spectinomycin and 10 mg/l tetracycline. This procedure selected transconjugants of Ea321T143 which contained various cosmids of the Ea321 library. After 48 hr of incubation at 28° C., freshly cut slices of immature pear fruit were pressed onto the surface of each plate of transconjugants such that all colonies beneath the pear-slice came in contact with pear tissue. The pear slices were inverted, incubated in plastic boxes lined with well-moistened paper towels and observed daily for up to 5 days for the presence of droplets of ooze. The immature pear fruit had been harvested approximately 6 weeks following bloom, from trees of Pyrus communis cv. Bartlett. The fruits were 2–4 cm in diameter, and they were stored at 0°–2° C. until used. Ooze as used in this description of the present invention, is a mixture of plant and bacterial products that consists largely of living bacterial cells.

The ooze was dilution-streaked on plates of *E. amylovora*-minimal medium with 50 μg/ml spectinomycin and 10 μgm/ml tetracycline, incubated for 2 days at 28° C. and individual colonies were picked with sterile toothpicks, propagated on a fresh plate of Ea minimal agar +50 μg/ml spectinomycin and 10 μgm/ml tetracycline and retested for pathogenicity. Freshly cut pear fruit tissue was stabbed with toothpicks contaminated with the strains to be tested. Cosmids from those colonies which caused disease on pear fruit were remobilized into DH5α from Ea321T143 by combining 0.5 aliquots of overnight LB +antibiotic cultures of DH5α, the Ea321T143 path⁺ transconjugant (the strain of Ea321T143 containing the cosmid which bestowed on Ea321T143 the ability to cause disease), and pRK2013, the helper plasmid. The combination was mixed thoroughly, centrifuged, and the pellet suspended in 150 μl of L broth, without antibiotics. The pellet was thoroughly resuspended and 0.1 ml drops were placed on LA plates, allowed to soak into the agar without spreading, and then the plates were incubated at 28° C. for 5 hr. After incubation, the spotted growth was resuspended in 1 ml of 5 mM potassium phosphate buffer, pH 6.5, and 0.1 aliquots were spread onto plates of LA +50 μg/ml spectinomycin and 20 μg/ml Naladixic acid, which were then incubated for 48 hr at 37° C. Colonies were simultaneously transferred with toothpicks to plates of LA +50 μg/ml spectinomycin and LA+Km. Those colonies that grew only on the 50 μg/ml spectinomycin plates, indicating loss of the helper plasmid pRK2013 ($Km^r$) were chosen for preservation by freezing and for further study.

To determine if the same cosmid that restored pathogenicity to pear, hereinafter referred to as pCPP430, also affected the reaction of Ea321T143 on tobacco, suspensions were infiltrated into tobacco leaf sectors. The effect of pCPP430, maintained in *E. coli* DH5α was tested in tobacco. The strain was grown to $OD_{620}$ 0.4–0.6 (approximately $10^8$ cfu/ml) in Luria broth +50 μg/ml spectinomycin. The culture was centrifuged (12,000 x g for 1 minute), resuspended in 5 mM phosphate buffer pH 6.5, to the original volume and infiltrated into tobacco leaves. Collapse of the tissue occurred within 8 hrs. No collapse was observed when cells of DH5α(alone) or DH5α(pCPP9) were infiltrated into tobacco leaves. Thus, we concluded that pCPP430, containing particular DNA of Ea321 enabled *E. coli* DH5α to cause the HR reaction and that pCPP430 contained all the genes necessary for this reaction.

The hrp gene from *E. amylovora* contained in the cosmid pCPP430, is particularly well expressed in *Escherichia coli* [see Advances in Molecular Genetics of Plant-Microbe Interactions, supra; Phytopathology 79:1166 (1989); and Mol. Plant-Microbe Interactions 4(5):493 (1991)]. Usually de novo RNA and protein synthesis was required for Ea321 to elicit the HR. However *E. coli*(pCPP430) and Ea321 (pCPP430) are able to elicit the HR in the presence of bacterial transcriptional or translational inhibitors such as rifampicin and tetracycline. This indicated that the HR elicitor was present in/on cells of *E. coli* DH5α(pCPP430) before tobacco leaves were infiltrated with the bacteria.

The search for the HR elicitor began by infiltrating tobacco leaves with the cell-free culture supernatants of *E. amylovora* Ea321, Ea321 (pCPP430) or *E. coli* DH5α (pCPP430). The supernatants were produced by growing each strain in LB broth with the appropriate antibiotic to late log phase ($O.D._{620}$=ca. 1.0). As we expected, based upon the experience of other workers [see Phytopathology 57:322 (1967)], no hypersensitive response occurred.

Strain Ea321 (pCPP430) was created by the following procedure:

EXAMPLE II

Strains Ea321, *E. coli* DH5α(pCPP430) and *E. coli* DH5α (pRK2013) were grown overnight in LB broth containing respectively, no antibiotic, 50 μg/ml spectinomycin, or $Km^{50}$. The next morning 0.5 ml aliquots of each strain were combined in a microcentrifuge tube, centrifuged for 2 min and resuspended in 0.15 ml of Luria broth (no antibiotics). A 0.1 ml aliquot of this suspension was spotted on Luria agar (no antibiotics) and incubated for 5 hr at 28° C. The growth from this spot was resuspended in 1 ml of 5 mM potassium phosphate buffer, pH 6.5, and 0.1 ml aliquots were spread on plates of *E. arnylovora* minimal medium containing 50 μg/ml spectinomycin to select for strains of Ea321 harboring pCPP430. Plates were incubated for 2–3 days at 28° C. Individual colonies were toothpicked simultaneously to minimal medium containing 50 μg/ml spectinomycin and to minimal medium containing $Km^{50}$. Only those colonies that grew on the medium with 50 μg/ml spectinomycin (indicating selection of pCPP430) but not on the medium with $Km^{50}$ (indicating loss of the helper plasmid pRK2013) were selected for further study.

Although cell-free culture supernatants of all bacteria used failed to elicit the hypersensitive response, preparations of certain cells in a new manner resulted in cell-free preparations that elicited a strong hypersensitive response within 12 hours that was indistinguishable from that elicited by whole metabolizing bacterial cells from which the preparations were made. The elicitor of the hypersensitive response was isolated, purified and characterized from this cell-free elicitor preparation (CFEP) according to Example III.

The isolation of CFEP containing harpin from *E. coli* DH5α(pcPP430) according to the present invention is described in the following example:

EXAMPLE III

Cells of *E. coli* DH5α(pCPP430) were grown in Luria-Bertani (LB) medium to $OD_{620}$=0.8 collected by centrifugation and resuspended in one tenth the original volume of 5 mM potassium phosphate buffer, pH 6.5, with 0.1 mM phenylmethylsulfonyl fluoride (PMSF), a serine protease inhibitor. The cells were then disrupted by sonication using a Sonicator Ultrasonic Cell Disruptor™ (Heat System-Ultrasonics) at a power output of 4, and the pulsar cycle timer set to 40% duty cycle (under these conditions, 10 ml of bacterial suspension were sonicated for 10 min on ice). After the debris from sonication were removed by centrifuging at 12,000 x g for 1 hour, the supernatant liquid was filtered through a 0.2 μm pore-size membrane filter to remove any remaining intact cells. The resulting preparation, at dilutions up to about 1:10, was able to elicit the hypersensitive response in tobacco leaves. The CFEP contained the intracellular material from a culture of $OD_{620}$= 0.4, the same density of living cells of *E. coli* required for elicitation of the hypersensitive response.

The purification of harpin according to the present example is described in the following example:

EXAMPLE IV

Initial experiments using the preparation obtained from Example III indicated that the HR-eliciting activity was heat stable and proteinaceous in nature. The preparation retained HR-eliciting activity as determined by infiltration of tobacco leaves as described previously following incubation overnight at 65° C. However, unless PMSF, the serine protease inhibitor, had been added during preparation, all HR-eliciting activity was lost after 3 hours at 37° C. or 6–8 hours at 4° C. Incubation of the preparation with Pronase E (Sigma) at 100 μg/ml, for 1 hour at 37° C. destroyed any elicitor activity.

The advantage of the heat stability of the elicitor preparation was used to aid in further purification of the elicitor. Only a limited number of proteins remained after holding the elicitor preparation of Example III in a boiling water bath for 10 minutes and subsequent removal of the insoluble material by centrifugation. One band, corresponding to 44 kD, was prominent following electrophoresis of the heated Example III preparation on SDS-polyacrylamide (10% SDS-PAGE gels were prepared and used according to instructions of the supplier, Hoeffer Scientific Instruments; protein in the gels was stained with 0.025% Coomassie Blue R-250 for 30 min and destained with 50% methanol and 10% acetic acid solution) gels. A band of this mobility was uniquely present in all preparations with HR-eliciting activity. Following resolution of the Example III preparation on an isoelectric-focusing granulated gel bed or by ion-exchange chromatography the fractions with HR-eliciting activity always contained a protein that corresponded to 44kD in molecular size with a pI of 4.0 to 4.5.

To accomplish further purification of harpin, several separation techniques were applied to CFEPs prepared as discussed in Example III. Before each step CFEP was heated in a boiling water bath for 10 minutes, cooled to 25°–30° C. and centrifuged for 10 min at 12,000 x g. The supernatant liquid was retained and filtered through a 0.2 μm pore size filtration membrane (Millipore, MF).

The heat-treated CFEP was bound to an anion exchange resin (Whatman DE-52) and eluted stepwise with increasing amounts of KCl in 5 mM potassium phosphate buffer, pH 6.5. Harpin was eluted from the column by buffer containing 90 mM KCl. The presence of harpin was determined by infiltration of tobacco leaf sectors with elements from the column that had been concentrated to 50% of the initial volume. In addition, fractions were electrophoresed in SDS-PAGE gels according to standard procedures. Final purification was accomplished by High Pressure Liquid Chromatography (HPLC). Preparations purified by ion-exchange chromatography were adjusted to pH 2 by the addition of acetic acid and, following centrifugation to remove any precipitates, were applied to a reverse-phase HPLC pre-packed column (YMC AQ-303). The column was eluted with a gradient of 10–70% acetonitrile at pH 2 in 0.25% w/v trifluoroacetic acid. Detection of protein was by absorption of light from 190 nm to 300 nm. Each 0.25 ml fraction was tested for ability to elicit the HR by infiltration of tobacco leaf sectors.

The granulated gel bed used for the resolution of the Example III preparation was prepared with Bio-lyte™ (Bio-Rad Laboratories) as recommended by the manufacturer. Wide-range ampholytes, pH 3–10 (Sigma) were used at a final concentration in the slurry of 2%. Electrode solutions were 1M $H_3PO_4$ (anode) and 1M NaOH (cathode).

To determine whether the prominent 44 kD protein ("harpin") band present in all HR-eliciting samples, had elicitor activity, the appropriate unstained region of a preparative SDS-gel was cut and electroeluted with buffer lacking SDS. The eluted protein (200 μg/ml) was dialyzed overnight against 2 liters of 5 mM potassium phosphate buffer, pH 6.5, containing 0.1 mM phenylmethyl sulfonyl fluoride. At concentrations $\geq$500 nM ($\geq$25 μg/ml), harpin elicited the hypersensitive response in leaves of all plants tested, including tobacco, tomato, and *Arabidopsis thaliana*.

Subsequent experimentation confirmed that harpin was protease sensitive, heat-stable, and acidic. Treatment of harpin with protease abolished HR-eliciting ability and eliminated the 44 kD protein band from SDS polyacrylamide gels. However, when harpin was incubated with protease that had been held at 100° C. for 10 min to inactivate the enzyme, the preparation retained HR-eliciting activity. When active protease was present in the infiltration mixture, no hypersensitive response developed. However, infiltration of tobacco leaves with active or heat-inactivated protease alone did not result in any macroscopic symptoms. Harpin retained its HR-eliciting activity following heating in a boiling water bath for 10 min. Purified harpin from an SDS gel had a pI of 4.3 as determined by resolution on thin-layer isoelectrofocusing gels using conventional techniques.

The subcellular location of harpin according to the present invention is described in the following example:

EXAMPLE V

The location of harpin on the organism's cell surface was suggested by the following observations: (i) the supernatant of *E. amylovora* Ea321 (pCPP430) or *E. coli* DH5α (pCPP430) did not elicit the hypersensitive response, indicating that harpin is not secreted into the medium but rather is present in or on the bacteria ; (ii) following incubation at 37° C. for 5 min of whole cells of Ea321(pCPP430) and *E. coli* DH5α(pCPP430) with 40 and 80 μg/ml of protease, respectively, and with 40 μg/ml tetracycline to halt the continued production of harpin, the bacteria failed to elicit a hypersensitive response. When 0.5 mM of PMSF, the protease inhibitor, was included in the above incubation mixture, the bacteria elicited the hypersensitive response; PMSF apparently protected harpin from inactivation by protease. (Infiltration of tobacco leaves with PMSF or tetracycline alone had no effect, indicating that neither compound functions independently in causing HR); (iii) treatment of bacteria with increasing amounts of protease resulted in decreased ability to elicit the hypersensitive response which correlates well with the disappearance of harpin from SDS gels in which preparations from the protease-treated bacteria had been electrophoresed [Table 1]; (iv) following centrifugation of the Example III preparation at 105,000 x g for 1 hr, most HR-eliciting activity was found in the supernatant liquid, however, when 30 mM MgCl$_2$, a membrane stabilizer, was added before sonication, most activity was associated with the pellet, that is with the centrifuged portion containing the membranes; and (v) gel-permeation chromatography of unboiled Example III preparation indicated association of the elicitor with a very high molecular weight (>10$^6$ D) fraction which were probably membrane vesicles; and (vi) fractionation of lysed cells of Ea321(pCPP430) [see Science 233:1403 (1985)] in the ultracentrifuge and reaction with a harpin-specific antibody, resulted only in reaction with the cell membrane faction and the whole cell control.

The foregoing results indicate that harpin is located at or near the bacterial cell-surface, and that it is unstable. Cell suspensions of Ea321(pCPP430) or *E. coli* DH5α (pCPP430) maintain their HR-eliciting activity for not more than 0.5 hr and 1 hr, respectively, in the presence of tetracycline (40 μg/ml), a translation inhibitor. In addition, harpin was not detected once the cells lost HR-eliciting activity. However, when the protease inhibitor PMSF (0.5 mM) was included in the suspension, the bacteria retained HR-eliciting activity for more than two hours, and decreasing amounts of harpin were detected simultaneously in the SDS gels over time. On an equal cell number basis, more protease was required to destroy harpin and prevent the hypersensitive reaction for *E. coli* DH5α(pCPP430) than for Ea321(pCPP430). Thus, the sensitivity of harpin to proteolysis may explain the previous observations of the short-lived nature of the HR-eliciting ability of phytopathogenic bacteria [see Science 245:1374 (1989)].

The following procedure and Table 1 depict the protocol for, and results of, protease sensitivity of HR-eliciting activity from *E. amylovora* Ea321 containing its hrp gene cluster.

Cells of *E. amylovora* Ea321 (pCPP430) were grown in LB medium and harvested at O.D.$_{620}$=0.6 by centrifugation. The cells were then resuspended in 0.1 volume of 5 mM potassium phosphate buffer, pH 6.5, containing 40 μg/ml tetracycline. Protease (as indicated in Table 1) was added to 200 μl cell suspension and incubated at 37° C. for 5 minutes and 100 μl of each mixture was subsequently infiltrated into tobacco leaves. Collapse was noted 24 hrs after infiltration. 20 μl of 5x cracking buffer was mixed with 80 μl of the remaining mixtures, boiled for 5 minutes and then centrifuged for 10 min in a microcentrifuge, prior to loading 15 μl in each lane of a 10% SDS-PAGE gel. Electrophoresis was carried out for 2 hours at 20 mA, followed by staining with 0.025% Coomassie Blue R-250 for 30 min and destaining with 50% methanol and 10% acetic acid solution. Cell-free supernatant, produced from the LB culture, was filter-sterilized and then concentrated to one tenth the original volume with the Centriprep-10 (Amicon). Treatment with the higher levels of protease resulted in loss of HR-eliciting ability and disappearance of the harpin band (44 kD) from the SDS gels. The resulting data from this protocol are reported in the following table:

TABLE 1

| Protease/ml | HR-elicitation on Tobacco | Harpin Detected |
|---|---|---|
| 0 μg | + | + |
| 5 μg | + | + |
| 10 μg | + | + |
| 20 μg | weak | + |
| 40 μg | − | − |
| 80 μg | − | − |
| 80 μg + 0.5 mM PMSF | + | + |
| cell-free supernatant | − | − |

+ = a positive reaction;
− = a negative reaction.

The ability of bacterial strains to elicit the hypersensitive response in intact tobacco leaves is strongly correlated with their ability to elicit a K$^+$/H$^+$ exchange reaction in tobacco cell suspension cultures. The two reactions are related genetically, as a major portion of hrp gene cluster of *E. amylovora* is needed for elicitation of the K$^+$/H$^+$ exchange reaction. Thus, the effect of harpin on tobacco cell suspension cultures was tested according to the following example.

The effect of harpin on plants, plant cells and tissues according to the present invention is described in the following example:

EXAMPLE VI

To determine if a particular preparation had HR-eliciting activity, we used a technique similar to that used with whole bacterial cells [see Mol. Plant-Microbe Interact. 4:494 (1991]. Tobacco plants (*Nicotiana tabacum* L. 'Xanthi') were grown in artificial soil mix to a height of 90–100 cm. Plants were moved from the greenhouse to the laboratory <24 hr before infiltration. Infiltration of the leaf lamina was done with a needle-less syringe through a small hole made with a dissecting needle. Collapse of the infiltrated area, indicative of the HR, was recorded 24 hrs after infiltration.

All CFEPs that contained the 44 kD protein, as detected by SDS-PAGE, caused collapses of the infiltrated areas of the tobacco leaves. Harpin, purified by HPLC (Example IV) elicited the HR at concentrations ≧500 nM.

To test the effect of harpin on tobacco cell suspension cultures, four-day old tobacco cell suspension cultures (*Nicotiana tabaccum* var. Samsun) were obtained from the Biotechnology Program at Cornell University. The cell suspension was filtered through a single layer of loose weave cheesecloth into a 1 liter beaker to eliminate any large clumped masses. Tobacco Assay Medium [MES 0.5 mM, mannitol 0.175 M, K$_2$SO$_4$ (2 ml of a 0.25 M stock solution), CaCl$_2$ (2 ml of a 0.25 M stock solution) high-purity water 996 ml; adjusted to pH 6.0 with 1N NaOH and filtered through a 0.2 μm pore-size membrane filter] was used to wash as many cells as possible through a single layer of cheesecloth. This washed and strained suspension was next poured into a large funnel lined with 1 layer of Miracloth™ (non-woven cloth), and the cells that lined the Miracloth™ were gently washed with an additional 200–400 ml of Tobacco Assay Medium. Fifteen gm of wet cells were weighed and gently resuspended in 415 ml of Tobacco Assay Medium. Twenty ml aliquots of this suspension were measured in to conical plastic cups (4 cm top diameter; 2.5 cm bottom diameter; 4 cm high) and immediately placed on a rotary shaker set at 150 rpm with a 2 cm stroke and maintained at 25°±3° C.

Cells were allowed to equilibrate until they reached a pH of approximately 5.8 (usually 20–30 min). At this point, 1 ml of bacterial suspension, or sonicated extract, or 0.5 ml of purified protein containing 20 μl of a 20 μg/ml concentrate of PMSF was added to each tobacco cell sample. The pH of the sample was read with a Corning pH meter and was adjusted back to pH 6 with 0.1 N NaOH (or 0.1 N HCl as needed). The second reading was taken 30 minutes after the first reading. All subsequent readings were taken at hourly intervals for up to 6 hours after the reading at time 0. All treatments were tested in duplicate.

Bacterial cell suspensions were prepared by growing overnight cultures in LB with the appropriate antibiotic and then diluting the strains back to an $OD_{620}$ of 0.20 the next morning. The cultures were regrown to OD 0.4. At this OD, strains of Ea321 and their derivatives are estimated to have a concentration of approximately $2 \times 10^8$ cfu/ml. Strains of *E. coli* DH5α and their derivatives are estimated to have a concentration of approximately $1 \times 10^8$ cfu/ml. The cells were centrifuged at 5000 x g and resuspended to give 5 fold concentrations (for Ea321 and derivatives) and 10 fold concentrations (for *E. coli* and derivatives) in 1 mM MES buffer pH 6. In this manner, cell concentrations of approximately $1 \times 10^9$ cfu/ml were achieved. When 1 ml of cell suspension was added to 20 ml tobacco cell suspension, the final concentration of cfu/ml for the assay was estimated at $5 \times 10^7$ per ml.

Figure 2:
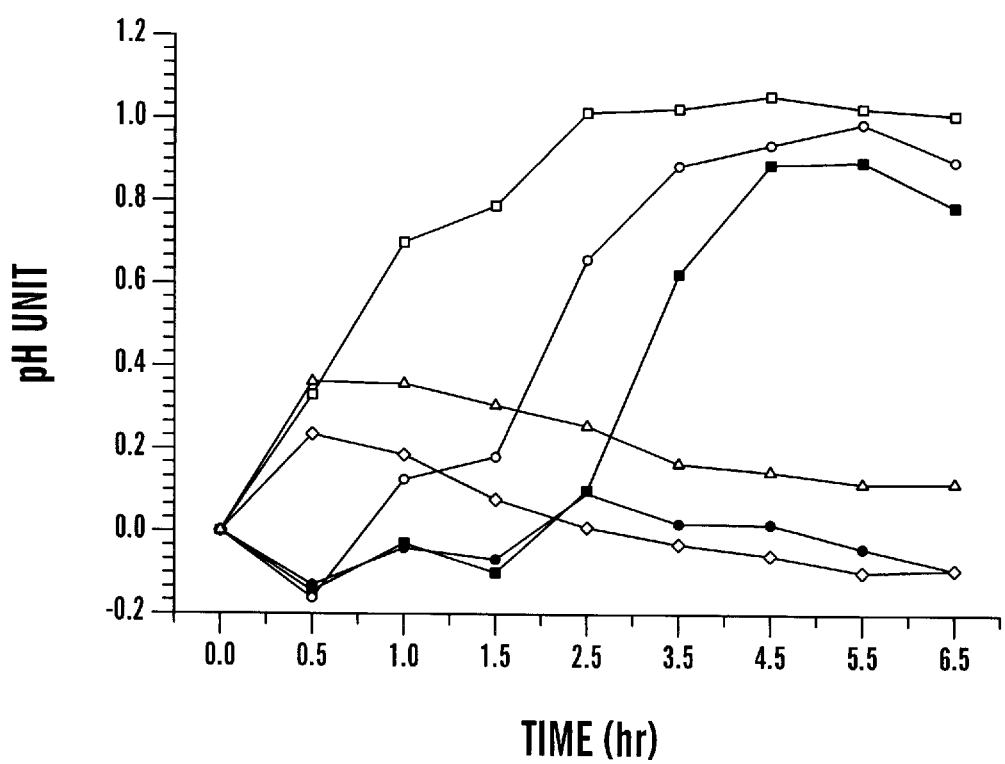

Cells of *E. amylovora* caused an increase in pH of the bathing solution (a measure of the $K^+/H^+$ exchange reaction) with a 2–3 hr delay following addition of bacteria to the tobacco cell suspension culture (see FIG. 2). In contrast, a one-time addition of harpin at time zero caused a rapid increase in the pH of the bathing solution during the first hour. The pH decreased slightly during subsequent incubation. Mutants of *E. amylovora* that do not produce harpin in vitro failed to elicit the $K^+/H^+$ exchange reaction. Strains of *E. coli* containing mutations in the cloned hrp gene cluster of *E. amylovora* also failed to elicit the exchange reaction. The elicitation of the exchange reaction, as well as the hypersensitive reaction, by harpin provides additional evidence that harpin is active in bacteria-plant interactions. The data from these studies on the effect of harpin on tobacco cell cultures is presented in FIG. 2.

The following example provides a comparison of harpin obtained from E. coli DH5α(pCPP430) and Ea 321.

EXAMPLE VII

To demonstrate that harpin is produced by *E. amylovora* and not *E. coli* stimulated by the presence of pCPP430, the same techniques used for its isolation from *E. coli* DH5α (pCPP430) were used with *E. amylovora* Ea321, except that the cells were preincubated in a HR-including medium for 5 hrs before sonication. In addition, *E. coli* DH5α(pCPP9), which harbors the vector of pCPP430, was subjected to the same procedures as *E.coli* DH5α(pCPP430). A protein isolated with the same molecular weight as that isolated from Ea321, had HR-eliciting ability. Based on the relative intensity of the 44 kD band on SDS polyacrylamide gels, it was estimated that *E. amylovora* Ea321 produces, on a per cell basis, about one tenth the amount of harpin as does *E. coli* DH5α(pCPP430). The properties of the elicitor protein from *E. amylovora* Ea321 and *E. coli* DH5α(pCPP430) were identical. No protease-sensitive heat stable HR-eliciting activity associated with a 44 kD protein was seen in cell-free extracts taken from *E. coli* DH5α(pCPP9).

The properties of the *E. amylovora* harpin are consistent with several important physiological observations that were made following the discovery that bacteria can elicit the hypersensitive response. Infiltration of plant tissues with incompatible pathogens and inhibitors of bacterial protein or RNA synthesis prevent the hypersensitive response [see Phytopathology 72:1513 (1982)] indicating that de novo RNA and protein synthesis is required. When bacteria are infiltrated in dilute water agar, no hypersensitive response is elicited, suggesting that intimate contact between bacteria and plant cells is required. Pre-induced bacteria quickly lose HR-eliciting ability when infiltrated with translation or transcriptional inhibitors [see Science 245:1374 (1989)]. Further evidence that the elicitor is a component of the bacterial cell surface is found in observations that the elicitor is not diffusible in infiltrated plant tissue and that each introduced bacterium kills only one plant cell. As predicted by these observations, harpin is associated with the bacterial cell surface and appears unstable in nature because of its extreme sensitivity to proteolysis. Thus, harpin degradation may be important in regulating the development of the plant-bacterium interaction.

The nonpathogenic phenotype of hrp mutants suggest that harpin is also a primary determinant of pathogenicity in *E. amylovora*. The basis for the essential role for harpin in both compatible (host:disease) and incompatible (nonhost:hypersensitive response) interactions is not clear. Host range in some plant pathogenic bacteria has been shown to be controlled by avr genes that can confer cultivar-specific incompatibility to $hrp^+$ pathogens. The biochemical activity of the avr gene products and the basis for their dependence on hrp genes for phenotypic expression is unknown, although avrB is regulated by hrp genes. Regulation of the production or accumulation of harpin may also be a determinative factor; the hrp gene cluster in *E. amylovora* is expressed about 10-fold lower in host tissue (pear) than in nonhost tissue (tobacco).

Although major disease determinants have been identified in plant pathogenic bacteria that cause either tumors or extensive tissue maceration (phytohormones and pectic enzymes, respectively), the molecular basis for pathogenicity among bacteria that cause delayed necrosis in a limited range of hosts is unknown. Among these bacteria are the economically important *Pseudomonas syringae* and *Xanthomonas campestris* pathovars. Toxins and plant cell wall degrading enzymes may increase the virulence of these pathogens, but the hrp genes are absolutely required for bacterial multiplication in host tissues and production of disease symptoms.

The conservation of the hrp genes [see Laby, R. J., Molecular studies on pathogenicity and virulence factors of *Erwinia amylovora*, M. S. Thesis, Cornell University (1991)] suggests that the *E. amylovora* harpin is the archetype of a broadly important class of plant bacterial disease determinants. Thus, disruption of harpin or of the proper balance of its production would be a novel approach to controlling the prevalent bacterial diseases of crop plants. The mode of action of harpin would also reveal the molecular bases for the hypersensitive response and for resistance of plants to a broad array of microbial pathogens.

The following example provides a description for the determination of the N-terminal amino acid sequence by which the gene encoding harpin was located.

EXAMPLE VIII

In order to locate the gene encoding harpin, named hrpN, the partial amino acid sequence of the harpin protein was determined. A sample of harpin (25 μg) purified by HPLC as in Example IV was used. A portion of the eluent from the reverse-phase chromatographic column corresponding to the peak eluting at 42.5 min was evaporated to near dryness in vacuo to eliminate the acetonitrile solvent. The fraction was then dissolved in TE buffer and submitted to the Protein Analysis Laboratory of the Cornell University Biotechnology Program with the request that the proportion of the various amino acids present in the protein, and the sequence of amino acids beginning from the N-terminus be determined.

The results of these analyses are shown in the following table in which the amino acid composition from analysis of harpin differs only slightly from the amino acid composition deduced from the DNA sequence:

| Amino Acid | % Deduced from DNA | % Deduced from Harpin |
|---|---|---|
| alanine | 5.4 | 7.6 |
| arginine | 1.8 | 1.3 |
| asparagine | 7.0 | |
| aspartic acid | 5.7 | 14.2 |
| cysteine | 0 | 0 |
| glutamine | 6.5 | |
| glutamic acid | 2.1 | 9.3 |
| glycine | 22.0 | 22.0 |
| histidine | 0.8 | <1.0 |
| isoleucine | 2.3 | 2.3 |
| leucine | 10.6 | 10.9 |
| lysine | 4.7 | 5.2 |
| methionine | 6.0 | 5.7 |
| phenylalanine | 1.6 | 2.0 |
| proline | 3.1 | 2.3 |
| serine | 9.6 | 8.9 |
| threonine | 6.2 | 5.2 |
| tryptophan | 0.5 | — |
| tyrosine | 1.0 | <1.0 |
| valine | 2.8 | 2.2 |

The procedures used for the determination of amino acid composition included hydrolysis of the protein with 6N HCL followed by derivitation of the amino acid residues and resolution according to S. A. Cohen et al., 1984, American Laboratory p. 48.

The N-terminal amino acid sequence of harpin according to the present invention was determined according to the methods of Hunkapiller [see Methods Of Protein Microcharacterization; A Practical Handbook, ppg 223–247, Humana Press, Clifton, N.J. (1986)] is as follows:

Met Ser Leu Asn Thr Ser Gly Leu Gly Ala Ser Thr Met Gln Ile
                5                   10                  15

The deduced amino acid sequence of harpin (including the N-terminal amino acid sequence given above) according to the present invention is:

Met Ser Leu Asn Thr Ser Gly Leu Gly Ala Ser Thr Met Gln Ile Ser
1           5                   10                  15

Ile Gly Gly Ala Gly Gly Asn Asn Gly Leu Leu Gly Thr Ser Arg Gln
            20                  25                  30

Asn Ala Gly Leu Gly Gly Asn Ser Ala Leu Gly Leu Gly Gly Gly Asn
            35              40                  45

Gln Asn Asp Thr Val Asn Gln Leu Ala Gly Leu Leu Thr Gly Met Met
            50              55              60

Met Met Met Ser Met Met Gly Gly Gly Gly Leu Met Gly Gly Gly Leu
65                  70                  75                  80

Gly Gly Gly Leu Gly Asn Gly Leu Gly Gly Ser Gly Gly Leu Gly Glu
                85                  90                  95

Gly Leu Ser Asn Ala Leu Asn Asp Met Leu Gly Gly Ser Leu Asn Thr
            100             105                 110

Leu Gly Ser Lys Gly Gly Asn Asn Thr Thr Ser Thr Thr Asn Ser Pro
            115             120                 125

Leu Asp Gln Ala Leu Gly Ile Asn Ser Thr Ser Gln Asn Asp Asp Ser
            130             135                 140

Thr Ser Gly Thr Asp Ser Thr Ser Asp Ser Ser Asp Pro Met Gln Gln
145             150                 155                 160

Leu Leu Lys Met Phe Ser Glu Ile Met Gln Ser Leu Phe Gly Asp Gly
                165                 170                 175

Gln Asp Gly Thr Gln Gly Ser Ser Ser Gly Gly Lys Gln Pro Thr Glu
                180                 185                 190

Gly Glu Gln Asn Ala Tyr Lys Lys Gly Val Thr Asp Ala Leu Ser Gly
                195             200             205

Leu Met Gly Asn Gly Leu Ser Gln Leu Leu Gly Asn Gly Gly Leu Gly
        210             215                 220

Gly Gly Gln Gly Gly Asn Ala Gly Thr Gly Leu Asp Gly Ser Ser Leu
225                 230                 235                 240

Gly Gly Lys Glu Leu Gln Asn Leu Ser Gly Pro Val Asp Tyr Gln Gln
            245                 250                 255

Leu Gly Asn Ala Val Gly Thr Gly Ile Gly Met Lys Ala Gly Ile Gln
                260             265                 270

Ala Leu Asn Asp Ile Gly Thr His Arg His Ser Ser Thr Arg Ser Phe
        275             280                 285

Val Asn Lys Gly Asp Arg Ala Met Ala Lys Glu Ile Gly Gln Phe Met
        290             295             300

Asp Gln Tyr Pro Glu Val Phe Gly Lys Pro Gln Tyr Gln Lys Gly Pro
305                 310                 315                 320

Gly Gln Glu Val Lys Thr Asp Asp Lys Ser Trp Ala Lys Ala Leu Ser
                325                 330             335

Lys Pro Asp Asp Asp Gly Met Thr Pro Ala Ser Met Glu Gln Phe Asn
            340                 345                 350

Lys Ala Lys Gly Met Ile Lys Arg Pro Met Ala Gly Asp Thr Gly Asn
            355             360             365

Gly Asn Leu Gln Ala Arg Gly Ala Gly Gly Ser Ser Leu Gly Ile Asp
        370             375             380

Ala Met Met Ala Gly Asp Ala Ile Asn Asn Met Ala Leu Gly Lys Leu
385             390                 395                 400

Gly Ala Ala

The partial amino acid sequence of harpin was utilized to contrsuct an oligonuceotide probe with bases corresponding to those encoding the ninth to fifteenth amino acids of the N-terminus of harpin. Since several of these amino acids may have several nucleic acid codons, a 48-fold degenerate oligonucleotide was to standard procedures.

The identification of clones encoding harpin by hybridization with an oligonucleotide probe for harpin is described in the following example:

EXAMPLE IX

The structural gene encoding harpin was identified by hybridization of the oligonucleotide probe constructed in Example VIII with DNA of *Erwinia amylovora*. The specific DNA cloned in the hrp cluster of *E. amylovora* in cosmid pCPP430 was digested with the restriction enzyme BamHI and a separate portion was digested with the restriction enzyme HindIII. The DNA digests were electrophoresed in 0.7% agarose, stained with ethidium bromide, transferred to a nylon membrane (Immobilon) and hybridized with the oligonucleotide probe previously described, according to standard procedures. The probe was labelled with radioactive phosphorous using $^{32}P$ labelled GTP.

Following hybridization and exposure of the membranes to X-O-Mat X-ray film (Kodak) and development of the film, a 1.3 kb HindIII fragment gave the strongest hybridization signal in response to the probe. The fragment was subcloned in the pBluescript M13+ vector (Stratagene), and designated pCPP1084.

The production of anti-harpin antibodies according to the present invention is described in the following example:

EXAMPLE X

Antibodies were raised in rabbits in response to injection with harpin. Three injections of highly purified harpin (100, 150 and 50 μg, respectively) were made at 2–3 week intervals. The antiserum was harvested after 8 weeks, IgG was precipitated with ammonium sulfate, and preabsorbed with sonicated E. coli DH5α(pCPP9) lysate. The specificity of the antiserum was confirmed by reaction in western blots of harpin purified by HPLC as described in Example VII. No reaction was seen with pre-immune serum when western blots containing resolved CFEP from DH5α(pCPP430) were hybridized.

The description of hrpN in the T7 RNA polymerase/promoter expression system is described in the following example:

EXAMPLE Xl

To confirm that the 1.3 kb HindIII fragment contains the entire hrpN gene, the plasmid pGpl-2 (Proc. Natl. Acad. Sci. U.S.A. 82:1074 (1985)) and pCPP1084, which contains the 1.3 kb HindIII fragment under the control of T7Φ10 promoter, was transformed, into E. coli DH5α or Ea321. These two compatible plasmids constitute the T7 expression system. The cells containing both pGpl-1 and pCPP1084 were grown in LB with 100 μg/ml of ampicillin and 50 μg/ml of kanamycin at 30° C. Two hundred μl of cells at $OD_{620}$=0.5 were harvested and washed with 5 ml of M9 media [Sambrook, J., E. F. Fritsch, T. Maniatis, Molecular Cloning. A Laboratory Manual, Second Edition, Cold Spring Harbor, (1989)]. Finally, the cells were resuspended in 1.0 ml of M9 medium supplemented with 0.01% of 18 amino acids (no cystidine or methionine). Cells were grown with shaking (200 rpm) at 30° C. for 1 hr then shifted to 42° C. for 10 min. Rifampicin (Sigma R35O1 20 mg/ml stock solution in methanol) was added to final concentration of 200 μg/ml. Cells were incubated at 42° C. for 10 additional minutes and then shifted to 30° C. and incubated for an additional 1 hour. Cells were pulsed with 10 μCi of $^{35}S$ methioine for 5 min at 30° C. The cells were centrifuged and resuspended in 50 μl of "cracking buffer" (60 mM Tris-HCl, pH 6.8, 1% SDS, 1% 2-mercaptoethanol, 10% glycerol and 0.01% bromophenol blue). The samples were heated at 100° C. for 3 min and 20 μl were placed on a 10% SDS PAGE gel. After electrophoresis at 15 mA for 2.0 hr in a Mighty Small™ apparatus (according to instruction of Hoefer Scientific Instruments), the gel was dried and exposed to X-ray film for 2 hrs at room temperature. A single 44 kD band, which corresponded in molecular size to harpin, was observed from both the E. coli DH5α and Ea321 constructs. The 44 kD band expressed from this system was also reacted with anti-harpin antibody raised in rabbit (Example X). This experiment demonstrated that the 1.3 kb HindIII fragment contains the entire open reading frame that encodes the 44 kD harpin protein.

The nucleic acid sequence of the hrpN gene according to the present invention was determined according to the following example.

EXAMPLE XII

DNA sequencing analysis was performed by the dideoxy-chain termination method (Sanger 1977, PNAS 74:5643–5667). The sequences were verified from both strands by using either the universal primer or the T3 primer. The subclones generated by Kpn1 and Pt+l from the 1.3 kb HindIII fragment were used directly as templates for sequencing. The nucleotide sequence of hrpN was submitted to Genbank and assigned accession number M92994. The nucleotide sequence is shown below.

```
AAGCTTCGGC ATGGCACGTT TGACCGTTGG GTCGGCAGGG TACGTTTGAA TTATTCATAA    60

GAGGAATACG TTATGAGTCT GAATACAAGT GGGCTGGGAG CGTCAACGAT GCAAATTTCT   120

ATCGGCGGTG CGGGCGGAAA TAACGGGTTG CTGGGTACCA GTCGCCAGAA TGCTGGGTTG   180

GGTGGCAATT CTGCACTGGG GCTGGGCGGC GGTAATCAAA ATGATACCGT CAATCAGCTG   240

GCTGGCTTAC TCACCGGCAT GATGATGATG ATGAGCATGA TGGGCGGTGG TGGGCTGATG   300

GGCGGTGGCT TAGGCGGTGG CTTAGGTAAT GGCTTGGGTG GCTCAGGTGG CCTGGGCGAA   360

GGACTGTCGA ACGCGCTGAA CGATATGTTA GGCGGTTCGC TGAACACGCT GGGCTCGAAA   420

GGCGGCAACA ATACCACTTC AACAACAAAT TCCCCGCTGG ACCAGGCGCT GGGTATTAAC   480

TCAACGTCCC AAAACGACGA TTCCACCTCC GGCACAGATT CCACCTCAGA CTCCAGCGAC   540
```

```
CCGATGCAGC AGCTGCTGAA GATGTTCAGC GAGATAATGC AAAGCCTGTT TGGTGATGGG  600

CAAGATGGCA CCCAGGGCAG TTCCTCTGGG GGCAAGCAGC CGACCGAAGG CGAGCAGAAC  660

GCCTATAAAA AAGGAGTCAC TGATGCGCTG TCGGGCCTGA TGGGTAATGG TCTGAGCCAG  720

CTCCTTGGCA ACGGGGGACT GGGAGGTGGT CAGGGCGGTA ATGCTGGCAC GGGTCTTGAC  780

GGTTCGTCGC TGGGCGGCAA AGGGCTGCAA AACCTGAGCG GGCCGGTGGA CTACCAGCAG  840

TTAGGTAACG CCGTGGGTAC CGGTATCGGT ATGAAAGCGG GCATTCAGGC GCTGAATGAT  900

ATCGGTACGC ACAGGCACAG TTCAACCCGT TCTTTCGTCA ATAAAGGCGA TCGGGCGATG  960

GCGAAGGAAA TCGGTCAGTT CATGGACCAG TATCCTGAGG TGTTTGGCAA GCCGCAGTAC 1020

CAGAAAGGCC CGGGTCAGGA GGTGAAAACC GATGACAAAT CATGGGCAAA AGCACTGAGC 1080

AAGCCAGATG ACGACGGAAT GACACCAGCC AGTATGGAGC AGTTCAACAA AGCCAAGGGC 1140

ATGATCAAAA GGCCCATGGC GGGTGATACC GGCAACGGCA ACCTGCAGGC ACGCGGTGCC 1200

GGTGGTTCTT CGCTGGGTAT TGATGCCATG ATGGCCGGTG ATGCCATTAA CAATATGGCA 1260

CTTGGCAAGC TGGGCGCGGC TTAAGCTT                                   1288
```

In this sequence, the open reading frame (including the stop codon TGA) which is expressed to provide the amino acid sequence for harpin is as follows:

```
ATGAGTCTGA ATACAAGTGG GCTGGGAGCG TCAACGATGC AAATTTCTAT CGGCGGTGCG   60

GGCGGAAATA ACGGGTTGCT GGGTACCAGT CGCCAGAATG CTGGGTTGGG TGGCAATTCT  120

GCACTGGGGC TGGGCGGCGG TAATCAAAAT GATACCGTCA ATCAGCTGGC TGGCTTACTC  180

ACCGGCATGA TGATGATGAT GAGCATGATG GGCGGTGGTG GGCTGATGGG CGGTGGCTTA  240

GGCGGTGGCT TAGGTAATGG CTTGGGTGGC TCAGGTGGCC TGGGCGAAGG ACTGTCGAAC  300

GCGCTGAACG ATATGTTAGG CGGTTCGCTG AACACGCTGG GCTCGAAAGG CGGCAACAAT  360

ACCACTTCAA CAACAAATTC CCCGCTGGAC CAGGCGCTGG GTATTAACTC AACGTCCCAA  420

AACGACGATT CCACCTCCGG CACAGATTCC ACCTCAGACT CCAGCGACCC GATGCAGCAG  480

CTGCTGAAGA TGTTCAGCGA GATAATGCAA AGCCTGTTTG GTGATGGGCA AGATGGCACC  540

CAGGGCAGTT CCTCTGGGGG CAAGCAGCCG ACCGAAGGCG AGCAGAACGC CTATAAAAAA  600

GGAGTCACTG ATGCGCTGTC GGGCCTGATG GGTAATGGTC TGAGCCAGCT CCTTGGCAAC  660

GGGGGACTGG GAGGTGGTCA GGGCGGTAAT GCTGGCACGG GTCTTGACGG TTCGTCGCTG  720

GGCGGCAAAG GGCTGCAAAA CCTGAGCGGG CCGGTGGACT ACCAGCAGTT AGGTAACGCC  780
```

-continued

```
GTGGGTACCG GTATCGGTAT GAAAGCGGGC ATTCAGGCGC TGAATGATAT CGGTACGCAC  840

AGGCACAGTT CAACCCGTTC TTTCGTCAAT AAAGGCGATC GGGCGATGGC GAAGGAAATC  900

GGTCAGTTCA TGGACCAGTA TCCTGAGGTG TTTGGCAAGC CGCAGTACCA GAAAGGCCCG  960

GGTCAGGAGG TGAAAACCGA TGACAAATCA TGGGCAAAAG CACTGAGCAA GCCAGATGAC  1020

GACGGAATGA CACCAGCCAG TATGGAGCAG TTCAACAAAG CCAAGGGCAT GATCAAAAGG  1080

CCCATGGCGG GTGATACCGG CAACGGCAAC CTGCAGGCAC GCGGTGCCGG TGGTTCTTCG  1140

CTGGGTATTG ATGCCATGAT GGCCGGTGAT GCCATTAACA ATATGGCACT TGGCAAGCTG  1200

GGCGCGGCT                                                         1209
```

The over expression of the hrpN gene to produce large quantities of harpin is depicted in the following example:

EXAMPLE XIII

A new plasmid designated pCPP50, was constructed especially for high expression of harpin as follows:.

The expression vector pINIII[113]-A2 [see Bio/Technology, pp 81–85 (Jan. 1984)] was modified. It was digested with the restriction endonuclease XbaI and HindIII which resulted in two fragments. The smaller DNA fragment was discarded and replaced with a portion of the pBluescript SK⁻ polylinker (XbaI to HindIII). These manipulations removed the ribosome-binding site and initiation codon (ATG) from pINIII[113]-A2 and replaced them with several useful cloning sites (XbaI, SpeI, BamHI, SmaI, PstI, EcoRV, HindIII, BamHI). The resulting vector (pCPP50) was used in conjunction with the hrpN gene to facilitate super-production of harpin by E. coli.

Plasmid pCPP1084, containing hrpN (Example VII) was digested with the restriction endonuclease HindIII. The 1.3 kb HindIII DNA fragment was purified from an agarose gel, and ligated into pCPP50 which had also been digested with HindIII and treated with alkaline phosphoratase. The DNA was transformed into E. coli DH5α. Several transformants were screened on an SDS-Polyacrylamide gel for production of a protein corresponding to the known mobility of harpin. One clone, designated pCPP2139, produced large quantities of harpin.

Large quantities of harpin were produced in E. coli DH5α(pCPP2139) according to the following procedure: E. coli DH5α(pCPP2139) was grown in M9 minimal medium supplemented with 5 g/l casamino acids and 40 mg/l thiamine. The bacteria were grown for an additional 20 hours at 37° C. Harpin was isolated from the bacteria according to Example III.

Harpin produced by E. coli DH5α(pCPP2139) was active in tobacco leaf assays and it had the same molecular weight on SDS-polyacrylamide gels and reacted with anti-harpin antiserum (Example X) as harpin produced by E. coli DH5α(pCPP430).

In dilution point tobacco leaf assays, CFEP produced from E. coli DH5α(pCPP2139) had detectable activity at a 1:150 dilution. E. coli DH5α(pCPP430) had detectable activity only to a 1:10 dilution. Thus, E. coli DH5α (pCPP2139) produced at least 15 times as much harpin as E. coli DH5α(pCPP430). The results referred to are tabulated in the following table.

TABLE 2

| CFEP from | Dilutions | | | | | |
|---|---|---|---|---|---|---|
| E. coli strain | 1:10 | 1:20 | 1:50 | 1:100 | 1:150 | 1:200 |
| DH5α(pCPP2139) | + | + | + | + | + | − |
| DH5α(pCPP430) | + | − | − | − | − | − |

+ = a positive reaction, collapse of tobacco tissue as in the hypersensitive response;
− = a negative reaction, no collapse of tobacco leaf tissue Similar conclusions were drawn by examination of SDS-polyacrylamide gels containing harpin preparations from the two constructions.

In addition to determining hrpN in E. amylovora, and because harpin is believed to be the archetype for a family of proteinaceous HR elicitors that are produced by many different phytopathogenic bacteria, the identification of hrpN homologs was also searched out in Erwinia chrysanthemi and Erwinia stewartii according to the following protocol.

EXAMPLE XIV

The 1.3 kb HindIII DNA fragment from pCPP1084, containing hrpN, was used as a radioactive probe against 18 cosmids previously shown to contain hrp genes from E. chrysanthemi strain AC4150. One cosmid, pCPP2157, hybridized strongly with the HrpN clone under high stringency conditions (washes done in 0.4 xSSC, o.2% SDS, 65° C.). The cosmid was used in further analyses. An 800 bp Cla1 fragment from pCPP2157, which hybridized with the HrpN probe, was cloned into pBluescript SK- to give pCPP2140. Initial DNA sequencing (using Sequenase version 2.0 kit, U.S. Biochemicals) of one end of the 800 bp Cla1 fragment showed a region of 224 nucleotides with 72% nucleotide identity. Sequence comparison was done with FASTA., and the nucleotide sequence for E. chrysanthemi corresponding to E. amylovora hrpN (best-fit) from nucleotide 1005 to 1223 indicates a 72% identity. The E. chrysantheni sequence is given below.

CGGTAAACCG GATACCAGAA AGATGGCTGG AGTTCGCCAG AAGACGGACG  50

ACAAATCCTG GGCTAAAGCG CTGAGTAAAC CGGATGATGA CGGTATGACC  100

GGTCTGCCAG CATGGACAAA TTCCGTCAGG CGATGGGTAT GATCAAAAGC  150

GCGGTGGCGG GTGATACCGG CAATACCAAC CTGAATCTGC GTGGCGCGGG  200

CGGTGCATCG CTGGGTATCG AT  222

Using a similar protocol, the 1.3 kb Hind III DNa fragment from pCPP1084 was used to probe a DNA of *E. stewartii*. Genomic DNA of strain DC283 and DNA of the cosmid clone pES411 [see Coplin et al., Mol. Plant-Microbe Interactions. 5:266–268 (1992)] were hydrolysed with Hind III, electrophoresed and hybridized. A 1.8 kb Hind III fragment from both DNA preparations hybridized with the probe. These results indicate that hrpN of *E. amylovora* shares homology with a hrpN-like gene of *E. stawartii*.

The effect of two means of inactivation, according to the present invention, of harpin on disease severity in plants is described below.

EXAMPLE XV

Inactivation of harpin by reaction of *E. amylovora* cells with an antiserum specific for harpin (Example X) or a protease that degrades harpin (Example VII) resulted in a reduction in disease of pear caused by *E. amylovora*. Immature pear fruit, harvested when the fruit were 3–4 cm in diameter were surface-disinfested, cut in half lengthwise and placed on moistened paper towels. Wells were cut in the cheeks of fruit with a number 1 cork borer (see Beer, S. V. Methods in Phytobacteriology, pp 372–375 (1990) Klement, Z., Rudolf, K, and Sands, D. eds). One ml of a culture of Ea321 ($2\times10^8$ cfu/ml) was mixed with 50 μl and 100 μl of a 1:25 dilution of anti-harpin antisera (Example X), and after 5 minutes, 50 μl of the mixture was deposited in the well of each pear fruit. Similarly, suspensions of Ea321 were mixed with protease before deposit in the wells in the pear fruit. The pears were incubated at 27° C. and observed daily for 3 days. Controls consisted of cells not treated and cells mixed with pre-immune serum taken from the same rabbit.

The results are tabulated below:

| Treatment | Infection* |
|---|---|
| Ea321 | 8/8 |
| Ea321 + Protease (100 μg/ml) | 6/8 |
| Ea321 + Protease (200 μg/ml) | 5/8 |
| Ea321 + Antiserum (50 μg/ml) | 5/8 |
| Ea321 + Antiserum (100 μg/ml) | 5/8 |
| Ea321 + Preimmune Serum (100 μg/ml) | 8/8 |

*Number of treated pear halves (out of 8) showing ooze at cut ends 64 hours after inoculation with 50 μl containing $1 \times 10^8$ cfu of Ea321 treated as indicated.

Treatment of *E. amylovora* with either protease or harpin-specific antiserum reduced the number of pear fruits that became infected. Treatment with preimmune (normal) serum had no effect on the development of disease. The above-described test of the effect of two treatments that affect harpin without affecting the vitality or growth of *E. amylovora* was particularly harsh. Only the harpin present on the treated cells could be affected because the antiserum or enzyme could not be present to react with harpin on the progeny from the treated cells. Under conditions envisioned for practical use according to the present invention, anti-harpin antibodies would be produced by plants transformed with genes encoding anti-harpin antibodies or protease, and these in turn would inhibit or lessen the disease severity of the plant exposed to the elicitor. Also, in nature, treatment of blooming apple or pear trees with protease or anti-harpin antibodies is likely to result in greater reductions in fire blight because infections generally are initiated by a small number of cells, as opposed to about $10^8$, as was used in the above example.

Thus, to summarize the present invention, there is strong evidence that harpin is the archetype for proteinaceous factors that enable plant pathogenic bacteria (and possibly other pathogenic microorganisms) to elicit either the hypersensitive response in nonhosts or to promote disease in hosts. To begin with, strains of the three genera *Erwinia*, *Pseudomonas*, and *Xanthomonas* elicit a very similar (visually and physiologically) hypersensitive response when infiltrated into leaves of their respective non-host plants. This relationship has been documented almost since the discovery of the hypersensitive response elicited by bacteria in 1963. In addition, the genes required for the elicitation of the HR by strains of all three genera of bacteria (referred to similarly, as hrp genes) are also those required for both pathogenicity to host plants and for elicitation of the hypersensitive response in non-host plants.

The relationship between hrp genes among phytopathogenic bacteria has been documented in studies by Laby and Beer [Molecular Plant Microbe Interactions 5:(1992); R. J. Laby, Molecular studies on pathogenicity and virulence factors of *Erwinia amylovora*, M. S. Thesis, Cornell University, Ithaca, N.Y. 1991]. They showed conclusively relationships, at the DNA level, between the hrp gene cluster of *E. amylovora* and the hrp gene cluster of *Pseudomonas syringae*, as well as the relationship between the hrp gene cluster of *E. amylovora* and the wts (water soaking) gene cluster of *E. stewartii*. Other workers have demonstrated a striking relationship among the hrp genes of various *P. syringae* pathovars (strains of *P. syringae* pathogenic to specific and different plants). Still other researchers have demonstrated a close relationship between hrp genes of strains of *Xanthomonas campestris* and *P. solanacearum*. Thus, there is overwhelming evidence for conserved DNA among plant pathogenic bacteria of several genera that cause disease of a multitude of plants.

The significant similarity in DNA sequence between the hrpN gene of *E. amylovora* and a homologous gene of *E. chrysanthemi*, according to the present invention, has also been shown. In addition, we have observed strong hybridization between hrpN and genomic DNA of *E. stewartii*, a serious pathogen of maize. More specifically, hybridization between hrpN and a specific 1.8 kb Hind III fragment of the wts gene cluster was observed. This indicates that the other two species of *Erwinia* examined to date have hrpN homologs. Thus, significant similarity in the hrpN-like gene products (protein) according to the present invention can be expected.

In addition, many of the hrp genes of *E. amylovora* appear to be involved in the secretion of cell-surface exposition of harpin, based on the phenotype of mutations in those genes. One gene of the hrp gene cluster of *Pseudomonas syringae*, which hybridizes with a portion of the hrp gene cluster of *E. amylovora*, encodes a protein with a high amino acid similarity with proteins involved in secretion in various Gram-negative bacteria.

Thus, the known similarities of hrp genes of *Pseudomonas, Xanthomnonas*, and *Erwinia* provide a firm basis to suspect that the HR elicitors produced by strains of the three genera are likely to be similar in amino acid sequence or at least in general characteristics (protein) and function.

The uses to which the various aspects and portions of the present invention may be put to are many and varied. For example, hrpN mutants may be used to identify, by complementation, genes from other plant pathogenic organisms (e.g., bacteria, fungi, nematodes) that encode proteins that function similarly to harpin. Although such proteins may have substantially different primary structures (and therefore would be difficult to detect by DNA hybridization techniques), these proteins should restore the ability to elicit the HR to either *E. amylovora* or *E. coli* cells carrying a hrp cluster that was functional, except for the hrpN gene.

Another use within the scope of the present invention is to use harpin and/or harpin-producing strains to identify in plants harpin receptors and/or their interactants in signal transduction pathways and clone their encoding genes. Thus, this would allow one to exploit the potential of harpin to function (depending upon the plant) as a pathogenicity factor or as an elicitor of defense reactions to manipulate the structure or expression of plant genes (s) encoding harpin receptor(s) for the purpose of producing genetically engineered plants with improved resistance to plant pathogens.

Still another use of harpin within the scope of the present invention would be as a potentiator of secondary metabolite production in plants grown either naturally or in tissue culture.

Still another use would be the fusion of the gene encoding harpin to specific promoters of plant genes to develop specific transgenic plants. When the plant gene is "turned on", harpin would be expressed and the plant cell killed. Some appropriate plant gene promoters and their projected uses include genes involved in pollen development (resulting in the development of male sterile plants); genes that are expressed in response to infection by fungi, e.g. genes encoding phenylalanine ammonia lyase and chalcone synthase (the plant cell would be killed thereby limiting the progress of the fungus and making the plant resistant to fungal diseases); and genes involved in the development of senescence (to facilitate harvest, expression of hrp genes would result in defoliation).

Still another use of harpin within the scope of the present invention would be the use of harpin as a "target molecule" with which chemical compounds would be designed to react and thereby inactivate the bacterial harpin, which, because it is essential for disease, would provide a specific bacteriacide target.

A listing of the nucleotide and amino acids described in the present application follows.

Thus while we have illustrated and described the preferred embodiment of our invention, it is to be understood that this invention is capable of variation and modification, and we therefore do not wish to be limited to the precise terms set forth, but desire to avail ourselves of such changes and alterations which may be made for adapting the invention to various usages and conditions. Such variations and modifications, for example, would include the substitution of structurally similar sequences, for both the elicitor and hrpN genes provided herein (whether derived from natural sources or synthetically manufactured), which function to yield substantially similar activities to those specifically described above. Thus, changes in sequence by the substitution, deletion, insertion or addition of nucleic acids (in the DNA sequences) or amino acids (in the peptide sequences) which do not substantially alter the function of those sequences specifically described above are deemed to be within the scope of the present invention. Accordingly, such changes and alterations are properly intended to be within the full range of equivalents, and therefore within the purview of the following claims.

We have described our invention and the manner and a process of making and using it in such full, clear, concise and exact terms so as to enable any person skilled in the art to which it pertains, or with which it is most nearly connected, to make and use the same.

We claim:

1. An isolated protein which elicits a hypersensitive response in different plant species when said protein is introduced into leaf tissue of a plant under normal plant growth condition, wherein said protein is encoded by a nucleic acid sequence which hybridizes to the nucleic acid of SEQ. ID. No. 4 under stringent conditions of 0.4 x SSC, 0.2% SDS washing at 65° C. or wherein said protein is protease sensitive and heat stable at 100° C. for at least one minute.

2. The isolated protein according to claim 1 which has a molecular size of 44 Kd and a pI of 4.3.

3. The isolated protein according to claim 1 which is a hypersensitive response elicitor protein from an *Erwinia*, *Pseudomonas*, or *Xanthomonas* pathogen.

4. The isolated peptide according to claim 1, wherein said protein is purified.

5. The isolated peptide according to claim 1, wherein said protein has no cysteine.

6. An isolated protein which elicits a hypersensitive response in different plant species when said protein is introduced into leaf tissue of a plant under normal plant growth conditions, wherein the hypersensitive response eliciting protein is from an Erwinia pathogen.

7. The isolated protein according to claim 6, wherein the Erwinia pathogen is *Erwinia amylovora.*

8. The isolated protein according to claim 7, wherein said protein has a molecular weight of 44 kDa as determined by SDS polyacrylamide gel electrophoresis.

9. The isolated protein according to claim 7, wherein said protein has an amino acid sequence of SEQ. ID. No. 2.

10. The isolated protein according to claim 6, wherein the Erwinia pathogen is *Erwinia chrysanthemi.*

11. The isolated protein according to claim 6, wherein the Erwinia pathogen is *Erwinia stewartii*.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide (xi) SEQUENCE DESCRIPTION: SEQ ID NO:1:

| Met | Ser | Leu | Asn | Thr | Ser | Gly | Leu | Gly | Ala | Ser | Thr | Met | Gln | Ile |
|-----|-----|-----|-----|-----|-----|-----|-----|-----|-----|-----|-----|-----|-----|-----|
| 1   |     |     |     | 5   |     |     |     |     | 10  |     |     |     |     | 15  |

(2) INFORMATION FOR SEQ ID NO:2:

(i) SEQUENCE CHARACTERISTICS:
        (A) LENGTH: 403 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

| Met | Ser | Leu | Asn | Thr | Ser | Gly | Leu | Gly | Ala | Ser | Thr | Met | Gln | Ile | Ser |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Ile | Gly | Gly | Ala | Gly | Gly | Asn | Asn | Gly | Leu | Leu | Gly | Thr | Ser | Arg | Gln |
|     |     |     | 20  |     |     |     |     | 25  |     |     |     |     | 30  |     |     |
| Asn | Ala | Gly | Leu | Gly | Gly | Asn | Ser | Ala | Leu | Gly | Leu | Gly | Gly | Gly | Asn |
|     |     |     |     | 35  |     |     |     |     | 40  |     |     |     |     | 45  |     |
| Gln | Asn | Asp | Thr | Val | Asn | Gln | Leu | Ala | Gly | Leu | Leu | Thr | Gly | Met | Met |
|     |     | 50  |     |     |     |     | 55  |     |     |     |     | 60  |     |     |     |
| Met | Met | Met | Ser | Met | Met | Gly | Gly | Gly | Gly | Leu | Met | Gly | Gly | Gly | Leu |
| 65  |     |     |     |     | 70  |     |     |     |     | 75  |     |     |     |     | 80  |
| Gly | Gly | Gly | Leu | Gly | Asn | Gly | Leu | Gly | Gly | Ser | Gly | Gly | Leu | Gly | Glu |
|     |     |     |     | 85  |     |     |     |     | 90  |     |     |     |     | 95  |     |
| Gly | Leu | Ser | Asn | Ala | Leu | Asn | Asp | Met | Leu | Gly | Gly | Ser | Leu | Asn | Thr |
|     |     |     | 100 |     |     |     |     | 105 |     |     |     |     | 110 |     |     |
| Leu | Gly | Ser | Lys | Gly | Gly | Asn | Asn | Thr | Thr | Ser | Thr | Thr | Asn | Ser | Pro |
|     |     |     | 115 |     |     |     |     | 120 |     |     |     |     | 125 |     |     |
| Leu | Asp | Gln | Ala | Leu | Gly | Ile | Asn | Ser | Thr | Ser | Gln | Asn | Asp | Asp | Ser |
|     |     | 130 |     |     |     |     | 135 |     |     |     |     | 140 |     |     |     |
| Thr | Ser | Gly | Thr | Asp | Ser | Thr | Ser | Asp | Ser | Ser | Asp | Pro | Met | Gln | Gln |
| 145 |     |     |     |     | 150 |     |     |     |     | 155 |     |     |     |     | 160 |
| Leu | Leu | Lys | Met | Phe | Ser | Glu | Ile | Met | Gln | Ser | Leu | Phe | Gly | Asp | Gly |
|     |     |     |     | 165 |     |     |     |     | 170 |     |     |     |     | 175 |     |
| Gln | Asp | Gly | Thr | Gln | Gly | Ser | Ser | Ser | Gly | Gly | Lys | Gln | Pro | Thr | Glu |
|     |     |     | 180 |     |     |     |     | 185 |     |     |     |     | 190 |     |     |
| Gly | Glu | Gln | Asn | Ala | Tyr | Lys | Lys | Gly | Val | Thr | Asp | Ala | Leu | Ser | Gly |
|     |     |     | 195 |     |     |     |     | 200 |     |     |     |     | 205 |     |     |
| Leu | Met | Gly | Asn | Gly | Leu | Ser | Gln | Leu | Leu | Gly | Asn | Gly | Gly | Leu | Gly |
|     |     | 210 |     |     |     |     | 215 |     |     |     |     | 220 |     |     |     |
| Gly | Gly | Gln | Gly | Gly | Asn | Ala | Gly | Thr | Gly | Leu | Asp | Gly | Ser | Ser | Leu |
| 225 |     |     |     |     | 230 |     |     |     |     | 235 |     |     |     |     | 240 |
| Gly | Gly | Lys | Gly | Leu | Gln | Asn | Leu | Ser | Gly | Pro | Val | Asp | Tyr | Gln | Gln |
|     |     |     |     | 245 |     |     |     |     | 250 |     |     |     |     | 255 |     |
| Leu | Gly | Asn | Ala | Val | Gly | Thr | Gly | Ile | Gly | Met | Lys | Ala | Gly | Ile | Gln |
|     |     |     | 260 |     |     |     |     | 265 |     |     |     |     | 270 |     |     |
| Ala | Leu | Asn | Asp | Ile | Gly | Thr | His | Arg | His | Ser | Ser | Thr | Arg | Ser | Phe |
|     |     |     | 275 |     |     |     |     | 280 |     |     |     |     | 285 |     |     |
| Val | Asn | Lys | Gly | Asp | Arg | Ala | Met | Ala | Lys | Glu | Ile | Gly | Gln | Phe | Met |
|     |     | 290 |     |     |     |     | 295 |     |     |     |     | 300 |     |     |     |
| Asp | Gln | Tyr | Pro | Glu | Val | Phe | Gly | Lys | Pro | Gln | Tyr | Gln | Lys | Gly | Pro |
| 305 |     |     |     |     | 310 |     |     |     |     | 315 |     |     |     |     | 320 |
| Gly | Gln | Glu | Val | Lys | Thr | Asp | Asp | Lys | Ser | Trp | Ala | Lys | Ala | Leu | Ser |
|     |     |     |     | 325 |     |     |     |     | 330 |     |     |     |     | 335 |     |

```
Lys  Pro  Asp  Asp  Asp  Gly  Met  Thr  Pro  Ala  Ser  Met  Glu  Gln  Phe  Asn
               340                    345                         350

Lys  Ala  Lys  Gly  Met  Ile  Lys  Arg  Pro  Met  Ala  Gly  Asp  Thr  Gly  Asn
          355                    360                         365

Gly  Asn  Leu  Gln  Ala  Arg  Gly  Ala  Gly  Gly  Ser  Ser  Leu  Gly  Ile  Asp
     370                    375                    380

Ala  Met  Met  Ala  Gly  Asp  Ala  Ile  Asn  Asn  Met  Ala  Leu  Gly  Lys  Leu
385                      390                    395                         400

Gly  Ala  Ala
```

(2) INFORMATION FOR SEQ ID NO:3:

(i) SEQUENCE CHARACTERISTICS:
        (A) LENGTH: 1288 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
AAGCTTCGGC  ATGGCACGTT  TGACCGTTGG  GTCGGCAGGG  TACGTTTGAA  TTATTCATAA      60
GAGGAATACG  TTATGAGTCT  GAATACAAGT  GGGCTGGGAG  CGTCAACGAT  GCAAATTTCT     120
ATCGGCGGTG  CGGGCGGAAA  TAACGGGTTG  CTGGGTACCA  GTCGCCAGAA  TGCTGGGTTG     180
GGTGGCAATT  CTGCACTGGG  GCTGGGCGGC  GGTAATCAAA  ATGATACCGT  CAATCAGCTG     240
GCTGGCTTAC  TCACCGGCAT  GATGATGATG  ATGAGCATGA  TGGGCGGTGG  TGGGCTGATG     300
GGCGGTGGCT  TAGGCGGTGG  CTTAGGTAAT  GGCTTGGGTG  GCTCAGGTGG  CCTGGGCGAA     360
GGACTGTCGA  ACGCGCTGAA  CGATATGTTA  GGCGGTTCGC  TGAACACGCT  GGGCTCGAAA     420
GGCGGCAACA  ATACCACTTC  AACAACAAAT  TCCCCGCTGG  ACCAGGCGCT  GGGTATTAAC     480
TCAACGTCCC  AAAACGACGA  TTCCACCTCC  GGCACAGATT  CCACCTCAGA  CTCCAGCGAC     540
CCGATGCAGC  AGCTGCTGAA  GATGTTCAGC  GAGATAATGC  AAAGCCTGTT  TGGTGATGGG     600
CAAGATGGCA  CCCAGGGCAG  TTCCTCTGGG  GGCAAGCAGC  CGACCGAAGG  CGAGCAGAAC     660
GCCTATAAAA  AAGGAGTCAC  TGATGCGCTG  TCGGGCCTGA  TGGGTAATGG  TCTGAGCCAG     720
CTCCTTGGCA  ACGGGGGACT  GGGAGGTGGT  CAGGGCGGTA  ATGCTGGCAC  GGGTCTTGAC     780
GGTTCGTCGC  TGGGCGGCAA  AGGGCTGCAA  AACCTGAGCG  GCCGGTGGA  CTACCAGCAG     840
TTAGGTAACG  CCGTGGGTAC  CGGTATCGGT  ATGAAAGCGG  GCATTCAGGC  GCTGAATGAT     900
ATCGGTACGC  ACAGGCACAG  TTCAACCCGT  TCTTTCGTCA  ATAAAGGCGA  TCGGGCGATG     960
GCGAAGGAAA  TCGGTCAGTT  CATGGACCAG  TATCCTGAGG  TGTTTGGCAA  GCCGCAGTAC    1020
CAGAAAGGCC  CGGGTCAGGA  GGTGAAAACC  GATGACAAAT  CATGGGCAAA  AGCACTGAGC    1080
AAGCCAGATG  ACGACGGAAT  GACACCAGCC  AGTATGGAGC  AGTTCAACAA  AGCCAAGGGC    1140
ATGATCAAAA  GGCCCATGGC  GGGTGATACC  GGCAACGGCA  ACCTGCAGGC  ACGCGGTGCC    1200
GGTGGTTCTT  CGCTGGGTAT  TGATGCCATG  ATGGCCGGTG  ATGCCATTAA  CAATATGGCA    1260
CTTGGCAAGC  TGGGCGCGGC  TTAAGCTT                                         1288
```

(2) INFORMATION FOR SEQ ID NO:4:

(i) SEQUENCE CHARACTERISTICS:
        (A) LENGTH: 1209 base pairs
        (B) TYPE: nucleic acid
        (C) STRANDEDNESS: single
        (D) TOPOLOGY: linear (  i  i  ) MOLECULE TYPE: cDNA ( x i ) SEQUENCE DESCRIPTION: SEQ ID NO:4:

| | | | | | | |
|---|---|---|---|---|---|---|
| ATGAGTCTGA | ATACAAGTGG | GCTGGGAGCG | TCAACGATGC | AAATTTCTAT | CGGCGGTGCG | 60 |
| GGCGGAAATA | ACGGGTTGCT | GGGTACCAGT | CGCCAGAATG | CTGGGTTGGG | TGGCAATTCT | 120 |
| GCACTGGGGC | TGGGCGGCGG | TAATCAAAAT | GATACCGTCA | ATCAGCTGGC | TGGCTTACTC | 180 |
| ACCGGCATGA | TGATGATGAT | GAGCATGATG | GGCGGTGGTG | GGCTGATGGG | CGGTGGCTTA | 240 |
| GGCGGTGGCT | TAGGTAATGG | CTTGGGTGGC | TCAGGTGGCC | TGGGCGAAGG | ACTGTCGAAC | 300 |
| GCGCTGAACG | ATATGTTAGG | CGGTTCGCTG | AACACGCTGG | GCTCGAAAGG | CGGCAACAAT | 360 |
| ACCACTTCAA | CAACAAATTC | CCCGCTGGAC | CAGGCGCTGG | GTATTAACTC | AACGTCCAA | 420 |
| AACGACGATT | CCACCTCCGG | CACAGATTCC | ACCTCAGACT | CCAGCGACCC | GATGCAGCAG | 480 |
| CTGCTGAAGA | TGTTCAGCGA | GATAATGCAA | AGCCTGTTTG | GTGATGGGCA | AGATGGCACC | 540 |
| CAGGGCAGTT | CCTCTGGGGG | CAAGCAGCCG | ACCGAAGGCG | AGCAGAACGC | CTATAAAAA | 600 |
| GGAGTCACTG | ATGCGCTGTC | GGGCCTGATG | GGTAATGGTC | TGAGCCAGCT | CCTTGGCAAC | 660 |
| GGGGGACTGG | GAGGTGGTCA | GGGCGGTAAT | GCTGGCACGG | GTCTTGACGG | TTCGTCGCTG | 720 |
| GGCGGCAAAG | GGCTGCAAAA | CCTGAGCGGG | CCGGTGGACT | ACCAGCAGTT | AGGTAACGCC | 780 |
| GTGGGTACCG | GTATCGGTAT | GAAAGCGGGC | ATTCAGGCGC | TGAATGATAT | CGGTACGCAC | 840 |
| AGGCACAGTT | CAACCCGTTC | TTTCGTCAAT | AAAGGCGATC | GGGCGATGGC | GAAGGAAATC | 900 |
| GGTCAGTTCA | TGGACCAGTA | TCCTGAGGTG | TTTGGCAAGC | CGCAGTACCA | GAAAGGCCCG | 960 |
| GGTCAGGAGG | TGAAAACCGA | TGACAAATCA | TGGGCAAAAG | CACTGAGCAA | GCCAGATGAC | 1020 |
| GACGGAATGA | CACCAGCCAG | TATGGAGCAG | TTCAACAAAG | CCAAGGGCAT | GATCAAAAGG | 1080 |
| CCCATGGCGG | GTGATACCGG | CAACGGCAAC | CTGCAGGCAC | GCGGTGCCGG | TGGTTCTTCG | 1140 |
| CTGGGTATTG | ATGCCATGAT | GGCCGGTGAT | GCCATTAACA | ATATGGCACT | TGGCAAGCTG | 1200 |
| GGCGCGGCT | | | | | | 1209 |

( 2 ) INFORMATION FOR SEQ ID NO:5:

( i ) SEQUENCE CHARACTERISTICS:
    ( A ) LENGTH: 220 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:5:

| | | | | | | |
|---|---|---|---|---|---|---|
| CGGTAAACCG | GATACCAGAA | AGATGGCTGG | AGTTCGCCAG | AAGACGGACG | ACAAATCCTG | 60 |
| GGCTAAAGCG | CTGAGTAAAC | CGGATGATGA | CGGTATGACC | GGTCTGCCAG | CATGGACAAA | 120 |
| TTCCGTCAGG | CGATGGGTAT | GATCAAAAGC | GCGGTGGCGG | GTGATACCGG | CAATACCAAC | 180 |
| CTGAATCTGC | GTGGCGCGGG | CGGTGCATCG | CTGGGTATCG | | | 220 |